US011800992B2

(12) United States Patent
Burnett

(10) Patent No.: US 11,800,992 B2
(45) Date of Patent: Oct. 31, 2023

(54) DEVICE AND METHOD FOR SAFE ACCESS AND AUTOMATED THERAPY

(71) Applicant: TheraNova, LLC, San Francisco, CA (US)

(72) Inventor: Daniel R. Burnett, San Francisco, CA (US)

(73) Assignee: TheraNova, LLC, San Francisco, CA (US)

( * ) Notice: Subject to any disclaimer, the term of this patent is extended or adjusted under 35 U.S.C. 154(b) by 20 days.

(21) Appl. No.: 15/993,483

(22) Filed: May 30, 2018

(65) Prior Publication Data
US 2018/0289536 A1    Oct. 11, 2018

Related U.S. Application Data

(63) Continuation of application No. 15/013,813, filed on Feb. 2, 2016, which is a continuation of application
(Continued)

(51) Int. Cl.
*A61B 5/06* (2006.01)
*A61M 1/28* (2006.01)
(Continued)

(52) U.S. Cl.
CPC ............ *A61B 5/068* (2013.01); *A61B 5/0022* (2013.01); *A61B 5/02055* (2013.01); *A61B 5/207* (2013.01); *A61B 5/208* (2013.01); *A61F 7/0085* (2013.01); *A61F 7/12* (2013.01); *A61M 1/28* (2013.01); *A61M 5/142* (2013.01); *A61M 5/1723* (2013.01); *A61B 5/024* (2013.01);
(Continued)

(58) Field of Classification Search
CPC ......... A61B 5/065; A61B 5/068; A61B 5/684; A61B 8/4245; A61B 8/4254; A61M 2039/0238; A61M 5/247; A61M 5/1723; A61M 5/172; A61M 25/0105; A61M 2025/0166; A61M 2005/1726
See application file for complete search history.

(56) References Cited

U.S. PATENT DOCUMENTS

| 2,078,786 A | 4/1937 | Wood |
| 3,042,042 A | 7/1962 | Blanck |

(Continued)

FOREIGN PATENT DOCUMENTS

| GB | 2267829 | 12/1993 |
| WO | WO 1992017150 | 10/1992 |

(Continued)

*Primary Examiner* — Jenna Zhang
(74) *Attorney, Agent, or Firm* — Levine Bagade Han LLP

(57) ABSTRACT

An automated therapy system having an infusion catheter; a sensor adapted to sense a patient parameter; and a controller communicating with the sensor and programmed to control flow output from the infusion catheter into a patient based on the patient parameter without removing fluid from the patient. The invention also includes a method of controlling infusion of a fluid to a patient. The method includes the following steps: monitoring a patient parameter with a sensor to generate a sensor signal; providing the sensor signal to a controller; and adjusting fluid flow to the patient based on the sensor signal without removing fluid from the patient.

37 Claims, 16 Drawing Sheets

Related U.S. Application Data

No. 13/937,102, filed on Jul. 8, 2013, now abandoned, which is a continuation of application No. 13/354,210, filed on Jan. 19, 2012, now Pat. No. 8,480,648, which is a continuation of application No. 12/098,365, filed on Apr. 4, 2008, now Pat. No. 8,100,880.

(60) Provisional application No. 60/921,974, filed on Apr. 5, 2007.

(51) Int. Cl.
    *A61M 5/142*   (2006.01)
    *A61M 5/172*   (2006.01)
    *A61B 5/20*    (2006.01)
    *A61F 7/12*    (2006.01)
    *A61F 7/00*    (2006.01)
    *A61B 5/00*    (2006.01)
    *A61B 5/0205*  (2006.01)
    *A61M 25/01*   (2006.01)
    *A61B 5/318*   (2021.01)
    *A61B 5/024*   (2006.01)
    *A61B 5/145*   (2006.01)

(52) U.S. Cl.
    CPC ......... *A61B 5/14507* (2013.01); *A61B 5/318* (2021.01); *A61F 2007/0022* (2013.01); *A61F 2007/0063* (2013.01); *A61F 2007/0093* (2013.01); *A61F 2007/126* (2013.01); *A61M 2025/0166* (2013.01); *A61M 2205/3303* (2013.01); *A61M 2230/04* (2013.01); *A61M 2230/10* (2013.01); *A61M 2230/202* (2013.01); *A61M 2230/205* (2013.01); *A61M 2230/208* (2013.01); *A61M 2230/65* (2013.01)

(56) References Cited

U.S. PATENT DOCUMENTS

| | | | |
|---|---|---|---|
| 3,505,988 A | | 4/1970 | Deane |
| 3,630,198 A | * | 12/1971 | Henkin ............ A61M 25/065 |
| | | | 604/170.01 |
| 3,698,396 A | | 10/1972 | Katerndahl et al. |
| 3,769,497 A | | 10/1973 | Frank |
| 3,927,980 A | | 12/1975 | Leonard |
| 4,302,972 A | | 12/1981 | Oettle et al. |
| 4,343,316 A | | 8/1982 | Jespersen |
| 4,356,826 A | * | 11/1982 | Kubota ................ A61B 5/03 |
| | | | 600/300 |
| 4,424,806 A | | 1/1984 | Newman et al. |
| 4,445,500 A | | 5/1984 | Osterholm |
| 4,450,841 A | | 5/1984 | Osterholm |
| 4,497,324 A | | 2/1985 | Sullivan et al. |
| 4,535,773 A | | 8/1985 | Yoon |
| 4,762,130 A | | 8/1988 | Fogarty et al. |
| 4,808,157 A | | 2/1989 | Coombs |
| 4,813,429 A | | 3/1989 | Eshel et al. |
| 4,836,214 A | | 6/1989 | Sramek |
| 4,883,459 A | | 11/1989 | Calderon |
| 4,904,237 A | | 2/1990 | Janese |
| 4,919,134 A | | 4/1990 | Streeter |
| 4,921,481 A | | 5/1990 | Danis et al. |
| 4,963,130 A | | 10/1990 | Osterholm |
| 5,108,364 A | | 4/1992 | Takezawa et al. |
| 5,122,267 A | | 6/1992 | Giovanetti et al. |
| 5,141,492 A | | 8/1992 | Dadson et al. |
| 5,141,493 A | | 8/1992 | Jacobsen et al. |
| 5,149,321 A | | 9/1992 | Klatz et al. |
| 5,188,618 A | | 2/1993 | Thomas |
| 5,199,442 A | * | 4/1993 | Seager ................ A61N 1/0512 |
| | | | 607/138 |
| 5,245,367 A | | 9/1993 | Miller et al. |
| 5,249,585 A | | 10/1993 | Turner et al. |
| 5,261,891 A | | 11/1993 | Brinkerhoff et al. |
| 5,263,485 A | | 11/1993 | Hickey |
| 5,344,136 A | | 9/1994 | Capdeboscq |
| 5,354,277 A | | 10/1994 | Guzman et al. |
| 5,380,160 A | | 1/1995 | Chen |
| 5,395,342 A | | 3/1995 | Yoon |
| 5,478,329 A | | 12/1995 | Ternamian |
| 5,554,280 A | | 9/1996 | Loehr |
| 5,562,821 A | | 10/1996 | Gutierrez |
| 5,623,940 A | | 4/1997 | Daikuzono |
| 5,665,227 A | | 9/1997 | Watt |
| 5,693,017 A | | 12/1997 | Spears et al. |
| 5,709,654 A | | 1/1998 | Klatz et al. |
| 5,709,661 A | | 1/1998 | Van Egmond et al. |
| 5,730,720 A | | 3/1998 | Sites et al. |
| 5,752,929 A | | 5/1998 | Klatz et al. |
| 5,755,668 A | | 5/1998 | Itoigawa et al. |
| 5,755,756 A | | 5/1998 | Freedman, Jr. et al. |
| 5,810,742 A | | 9/1998 | Pearlman |
| 5,837,003 A | | 11/1998 | Ginsburg |
| 5,891,035 A | | 4/1999 | Wood et al. |
| 5,951,497 A | | 9/1999 | Wallace et al. |
| 6,019,729 A | | 2/2000 | Itoigawa et al. |
| 6,019,783 A | | 2/2000 | Philips et al. |
| 6,056,766 A | | 5/2000 | Thompson et al. |
| 6,066,163 A | | 5/2000 | John |
| 6,117,076 A | | 9/2000 | Cassidy |
| 6,122,536 A | | 9/2000 | Sun et al. |
| 6,126,684 A | | 10/2000 | Gobin et al. |
| 6,146,411 A | | 11/2000 | Noda et al. |
| 6,149,624 A | | 11/2000 | McShane |
| 6,149,670 A | | 11/2000 | Worthen et al. |
| 6,165,207 A | | 12/2000 | Balding et al. |
| 6,175,688 B1 | | 1/2001 | Cassidy et al. |
| 6,188,930 B1 | | 2/2001 | Carson |
| 6,197,045 B1 | | 3/2001 | Carson |
| 6,231,524 B1 | | 5/2001 | Wallace et al. |
| 6,231,594 B1 | | 5/2001 | Dae |
| 6,254,567 B1 | | 7/2001 | Treu et al. |
| 6,261,312 B1 | | 7/2001 | Dobak et al. |
| 6,264,680 B1 | | 7/2001 | Ash |
| 6,287,326 B1 | | 9/2001 | Pecor |
| 6,290,717 B1 | | 9/2001 | Philips |
| 6,299,599 B1 | | 10/2001 | Pham et al. |
| 6,304,776 B1 | | 10/2001 | Muntermann |
| 6,312,452 B1 | | 11/2001 | Dobak et al. |
| 6,334,064 B1 | | 12/2001 | Fiddian-green |
| 6,336,910 B1 | | 1/2002 | Ohta et al. |
| 6,337,994 B1 | | 1/2002 | Stoianovici et al. |
| 6,338,727 B1 | | 1/2002 | Noda et al. |
| 6,357,447 B1 | | 3/2002 | Swanson et al. |
| 6,368,304 B1 | | 4/2002 | Aliberto et al. |
| 6,375,674 B1 | | 4/2002 | Carson |
| 6,379,331 B2 | | 4/2002 | Barbut et al. |
| 6,405,080 B1 | | 6/2002 | Lasersohn et al. |
| 6,409,699 B1 | | 6/2002 | Ash |
| 6,419,643 B1 | | 7/2002 | Shimada et al. |
| 6,436,295 B2 | | 8/2002 | Kim |
| 6,447,474 B1 | | 9/2002 | Balding |
| 6,450,990 B1 | | 9/2002 | Walker et al. |
| 6,451,045 B1 | | 9/2002 | Walker et al. |
| 6,458,150 B1 | | 10/2002 | Evans et al. |
| 6,460,544 B1 | | 10/2002 | Worthen |
| 6,461,379 B1 | | 10/2002 | Carson et al. |
| 6,480,257 B2 | | 11/2002 | Cassidy et al. |
| 6,497,721 B2 | | 12/2002 | Ginsburg et al. |
| 6,520,933 B1 | | 2/2003 | Evans et al. |
| 6,529,775 B2 | | 3/2003 | Whitebook et al. |
| 6,530,945 B1 | | 3/2003 | Noda et al. |
| 6,530,946 B1 | | 3/2003 | Noda et al. |
| 6,547,811 B1 | | 4/2003 | Becker et al. |
| 6,551,302 B1 | | 4/2003 | Rosinko et al. |
| 6,554,797 B1 | | 4/2003 | Worthen |
| 6,572,640 B1 | | 6/2003 | Balding et al. |
| 6,579,496 B1 | | 6/2003 | Fausset et al. |
| 6,581,403 B2 | | 6/2003 | Whitebook et al. |
| 6,582,398 B1 | | 6/2003 | Worthen et al. |
| 6,585,692 B1 | | 7/2003 | Worthen |
| 6,592,577 B2 | | 7/2003 | Abboud et al. |

(56) References Cited

U.S. PATENT DOCUMENTS

| | | |
|---|---|---|
| 6,592,612 B1 | 7/2003 | Samson et al. |
| 6,602,243 B2 | 8/2003 | Noda |
| 6,620,187 B2 | 9/2003 | Carson et al. |
| 6,620,189 B1 | 9/2003 | Machold et al. |
| 6,632,196 B1 | 10/2003 | Houser |
| 6,635,053 B1 | 10/2003 | Lalonde et al. |
| 6,638,265 B1 | 10/2003 | Ternamian |
| 6,641,602 B2 | 11/2003 | Balding |
| 6,641,603 B2 | 11/2003 | Walker et al. |
| 6,645,232 B2 | 11/2003 | Carson |
| 6,645,234 B2 | 11/2003 | Evans et al. |
| 6,648,905 B2 | 11/2003 | Hoglund et al. |
| 6,660,027 B2 | 12/2003 | Gruszecki et al. |
| 6,669,715 B2 | 12/2003 | Hoglund et al. |
| 6,673,098 B1 | 1/2004 | Machold et al. |
| 6,676,409 B2 | 1/2004 | Grant |
| 6,676,689 B2 | 1/2004 | Dobak et al. |
| 6,682,551 B1 | 1/2004 | Worthen et al. |
| 6,685,733 B1 | 2/2004 | Dae et al. |
| 6,692,518 B2 | 2/2004 | Carson |
| 6,692,519 B1 | 2/2004 | Hayes, Jr. |
| 6,695,873 B2 | 2/2004 | Dobak et al. |
| 6,695,874 B2 | 2/2004 | Machold et al. |
| 6,699,267 B2 | 3/2004 | Voorhees et al. |
| 6,699,268 B2 | 3/2004 | Kordis et al. |
| 6,702,842 B2 | 3/2004 | Hoglund et al. |
| 6,704,590 B2 | 3/2004 | Haldeman |
| 6,706,060 B2 | 3/2004 | Tzeng et al. |
| 6,709,448 B2 | 3/2004 | Walker et al. |
| 6,716,236 B1 | 4/2004 | Tzeng et al. |
| 6,719,724 B1 | 4/2004 | Walker et al. |
| 6,723,053 B2 | 4/2004 | Ackerman et al. |
| 6,733,517 B1 | 5/2004 | Collins |
| 6,740,109 B2 | 5/2004 | Dobak |
| 6,743,218 B2 | 6/2004 | Maginot et al. |
| 6,746,474 B2 | 6/2004 | Saadat |
| 6,749,625 B2 | 6/2004 | Pompa et al. |
| 6,752,786 B2 | 6/2004 | Callister |
| 6,764,391 B1 | 7/2004 | Grant et al. |
| 6,796,995 B2 | 9/2004 | Pham et al. |
| 6,799,063 B2 | 9/2004 | Carson |
| 6,800,068 B1 | 10/2004 | Dae et al. |
| 6,802,855 B2 | 10/2004 | Ellingboe et al. |
| 6,807,444 B2 | 10/2004 | Tu et al. |
| 6,811,551 B2 | 11/2004 | Dae et al. |
| 6,818,012 B2 | 11/2004 | Ellingboe |
| 6,819,950 B2 | 11/2004 | Mills |
| 6,827,728 B2 | 12/2004 | Ellingboe et al. |
| 6,827,898 B1 | 12/2004 | Fausset et al. |
| 6,872,222 B2 | 3/2005 | Luo et al. |
| 6,878,156 B1 | 4/2005 | Noda |
| 6,887,262 B2 | 5/2005 | Dobak et al. |
| 6,887,263 B2 | 5/2005 | Bleam et al. |
| 6,893,454 B2 | 5/2005 | Collins |
| 6,921,198 B2 | 7/2005 | Gruszecki et al. |
| 6,974,463 B2 | 12/2005 | Magers et al. |
| 6,981,945 B1 | 1/2006 | Sarvazyan et al. |
| 7,001,418 B2 | 2/2006 | Noda |
| 7,008,444 B2 | 3/2006 | Dae et al. |
| 7,018,399 B2 | 3/2006 | Dobak et al. |
| 7,063,718 B2 | 6/2006 | Dobak |
| 7,070,612 B1 | 7/2006 | Collins et al. |
| 7,077,825 B1 | 7/2006 | Stull |
| 7,090,792 B1 | 8/2006 | Balding et al. |
| 7,097,657 B2 | 8/2006 | Noda et al. |
| 7,144,407 B1 | 12/2006 | Lasersohn |
| 7,172,586 B1 | 2/2007 | Dae et al. |
| 7,181,927 B2 | 2/2007 | Collins et al. |
| 7,255,709 B2 | 8/2007 | Walker et al. |
| 7,264,680 B2 | 9/2007 | Gebhart et al. |
| 7,276,046 B1 | 10/2007 | Suzuki et al. |
| 7,278,984 B2 | 10/2007 | Noda et al. |
| 7,287,398 B2 | 10/2007 | Noda et al. |
| 7,294,142 B2 | 11/2007 | Dobak et al. |
| 7,300,453 B2 | 11/2007 | Yon |
| 7,311,724 B1 | 12/2007 | Ginsburg |
| 7,311,725 B2 | 12/2007 | Dobak |
| 7,361,186 B2 | 4/2008 | Voorhees et al. |
| 7,371,254 B2 | 5/2008 | Dobak |
| 7,381,190 B2 | 6/2008 | Sugure et al. |
| 7,407,487 B2 | 8/2008 | Dae et al. |
| 7,425,216 B2 | 9/2008 | Collins |
| 7,458,984 B2 | 12/2008 | Yon et al. |
| 7,491,223 B2 | 2/2009 | Lasheras |
| 7,566,341 B2 | 7/2009 | Keller et al. |
| 7,640,768 B2 | 1/2010 | Noda et al. |
| 7,666,213 B2 | 2/2010 | Freedman, Jr. et al. |
| 7,666,215 B2 | 2/2010 | Callister et al. |
| 7,713,241 B2 | 5/2010 | Cartledge et al. |
| 7,771,460 B2 | 8/2010 | Ginsburg et al. |
| 7,818,155 B2 | 10/2010 | Stuebe et al. |
| 7,819,835 B2 | 10/2010 | Landy et al. |
| 7,824,436 B2 | 11/2010 | Barbut et al. |
| 7,827,005 B2 | 11/2010 | Kimball |
| 7,842,002 B2 | 11/2010 | Mantle |
| 7,922,738 B2 | 4/2011 | Eichmann et al. |
| 8,100,880 B2 | 1/2012 | Burnett et al. |
| 8,147,486 B2 | 4/2012 | Honour et al. |
| 8,439,960 B2 | 5/2013 | Burnett et al. |
| 8,480,648 B2 | 7/2013 | Burnett et al. |
| 8,535,237 B2 | 9/2013 | Nishtala |
| 8,613,702 B2 | 12/2013 | Feer et al. |
| 8,814,807 B2 | 8/2014 | Hulvershorn et al. |
| 8,926,525 B2 | 1/2015 | Hulvershorn et al. |
| 8,986,230 B2 | 3/2015 | Nishtala |
| 9,179,971 B2 | 11/2015 | Kirschenman |
| 9,220,483 B2 | 12/2015 | Frankhouser et al. |
| 9,226,878 B2 | 1/2016 | Elia et al. |
| 9,238,126 B2 | 1/2016 | Gerrans et al. |
| 9,295,395 B2 | 3/2016 | Elia et al. |
| 9,532,739 B2 | 1/2017 | Bennett-guerrero |
| 9,610,227 B2 | 4/2017 | Elia |
| 9,622,670 B2 | 4/2017 | Burnett et al. |
| 9,642,779 B2 | 5/2017 | Elia et al. |
| 9,713,579 B2 | 7/2017 | Elia et al. |
| 2002/0026094 A1 | 2/2002 | Roth |
| 2002/0033181 A1 | 3/2002 | Groth et al. |
| 2002/0147481 A1 | 10/2002 | Brugger et al. |
| 2002/0161314 A1 | 10/2002 | Sarajarvi |
| 2003/0018279 A1 | 1/2003 | Rosenblatt |
| 2003/0050621 A1 | 3/2003 | Lebel et al. |
| 2003/0088186 A1* | 5/2003 | Doody ............... A61B 5/6848 600/587 |
| 2003/0088290 A1 | 5/2003 | Spinelli et al. |
| 2003/0131844 A1 | 7/2003 | Kumar et al. |
| 2003/0135087 A1 | 7/2003 | Hickle et al. |
| 2004/0087606 A1 | 5/2004 | Voorhees et al. |
| 2004/0102826 A1 | 5/2004 | Lasheras et al. |
| 2004/0122353 A1 | 6/2004 | Shahmirian et al. |
| 2004/0138701 A1 | 7/2004 | Haluck |
| 2004/0147871 A1 | 7/2004 | Burnett |
| 2004/0158119 A1 | 8/2004 | Osorio et al. |
| 2004/0172116 A1 | 9/2004 | Seifert et al. |
| 2004/0193098 A1 | 9/2004 | Wentling et al. |
| 2004/0231664 A1 | 11/2004 | Lurie et al. |
| 2005/0033391 A1 | 2/2005 | Worthen et al. |
| 2005/0172212 A1 | 8/2005 | Birsa et al. |
| 2005/0177212 A1 | 8/2005 | Njemanze |
| 2005/0203598 A1 | 9/2005 | Becker et al. |
| 2006/0025839 A1 | 2/2006 | Gonzales |
| 2006/0064146 A1 | 3/2006 | Collins |
| 2006/0100743 A1 | 5/2006 | Townsend et al. |
| 2006/0161107 A1 | 7/2006 | Mantle |
| 2006/0173480 A1 | 8/2006 | Zhang |
| 2006/0190066 A1 | 8/2006 | Worthen |
| 2006/0276864 A1 | 12/2006 | Collins |
| 2006/0282039 A1 | 12/2006 | Duong et al. |
| 2006/0293734 A1 | 12/2006 | Scott et al. |
| 2007/0016007 A1* | 1/2007 | Govari ............... A61B 5/063 600/424 |
| 2007/0027393 A1 | 2/2007 | Williams et al. |
| 2007/0045188 A1 | 3/2007 | Blanton |
| 2007/0051409 A1 | 3/2007 | Landy et al. |
| 2007/0106247 A1 | 5/2007 | Burnett et al. |

(56) References Cited

U.S. PATENT DOCUMENTS

| | | |
|---|---|---|
| 2007/0173755 A1 | 7/2007 | Alimi et al. |
| 2007/0203552 A1 | 8/2007 | Machold et al. |
| 2007/0225781 A1 | 9/2007 | Saadat et al. |
| 2007/0244446 A1 | 10/2007 | Sundar et al. |
| 2008/0045867 A1 | 2/2008 | Jensen et al. |
| 2008/0077088 A1 | 3/2008 | Collins |
| 2008/0077206 A1 | 3/2008 | Collins |
| 2008/0097179 A1 | 4/2008 | Russo |
| 2008/0103408 A1 | 5/2008 | Denton et al. |
| 2008/0119757 A1 | 5/2008 | Winter |
| 2008/0119788 A1 | 5/2008 | Winter |
| 2008/0147040 A1* | 6/2008 | Dikshteyn ............ A61B 5/287 600/300 |
| 2008/0154197 A1 | 6/2008 | Derrico et al. |
| 2008/0156092 A1 | 7/2008 | Boiarski |
| 2008/0167607 A1 | 7/2008 | Pfeiffer et al. |
| 2008/0200863 A1 | 8/2008 | Chomas et al. |
| 2008/0234619 A1 | 9/2008 | Fausset et al. |
| 2008/0249467 A1* | 10/2008 | Burnett ............ A61B 17/3417 604/117 |
| 2008/0255644 A1 | 10/2008 | Carson |
| 2009/0076573 A1 | 3/2009 | Burnett et al. |
| 2009/0099629 A1 | 4/2009 | Carson et al. |
| 2009/0124937 A1 | 5/2009 | Parks |
| 2009/0131835 A1 | 5/2009 | Voorhees et al. |
| 2009/0240312 A1 | 9/2009 | Koewler |
| 2009/0312676 A1 | 12/2009 | Rousso et al. |
| 2010/0152616 A1 | 6/2010 | Beyhan et al. |
| 2010/0204765 A1 | 8/2010 | Hall et al. |
| 2010/0249663 A1 | 9/2010 | Nishtala |
| 2010/0286559 A1 | 11/2010 | Paz et al. |
| 2010/0305656 A1 | 12/2010 | Imran et al. |
| 2011/0046547 A1 | 2/2011 | Mantle |
| 2012/0016256 A1 | 1/2012 | Mabary et al. |
| 2012/0059340 A1 | 3/2012 | Larsson |
| 2012/0116487 A1 | 5/2012 | Burnett et al. |
| 2012/0271372 A1 | 10/2012 | Osorio |
| 2012/0277619 A1 | 11/2012 | Starkebaum et al. |
| 2013/0030262 A1 | 1/2013 | Burnett et al. |
| 2013/0066166 A1 | 3/2013 | Burnett et al. |
| 2013/0225946 A1 | 8/2013 | Feer et al. |
| 2013/0226077 A1 | 8/2013 | Burnett et al. |
| 2013/0296984 A1 | 11/2013 | Burnett et al. |
| 2014/0031631 A1 | 1/2014 | Hall et al. |
| 2014/0056325 A1 | 2/2014 | Guerra et al. |
| 2014/0228781 A1 | 8/2014 | Boyle et al. |
| 2015/0328081 A1 | 11/2015 | Goldenberg et al. |
| 2016/0113843 A1 | 4/2016 | Elia et al. |
| 2016/0129223 A1 | 5/2016 | Kirschenman |
| 2017/0202750 A1 | 7/2017 | Elia |
| 2018/0161249 A1 | 6/2018 | Elia et al. |

FOREIGN PATENT DOCUMENTS

| | | |
|---|---|---|
| WO | WO 2000/048670 | 8/2000 |
| WO | WO 2000/072779 | 12/2000 |
| WO | WO 2001/003606 | 1/2001 |
| WO | WO 2001/017471 | 3/2001 |
| WO | WO 2001/041708 | 6/2001 |
| WO | WO 2002/026175 | 4/2002 |
| WO | WO 2002/026176 | 4/2002 |
| WO | WO 2009/071094 | 6/2009 |
| WO | WO 2009/071095 | 6/2009 |
| WO | WO 2009/071096 | 6/2009 |
| WO | WO 2009/071097 | 6/2009 |
| WO | WO 2009/071098 | 6/2009 |

* cited by examiner

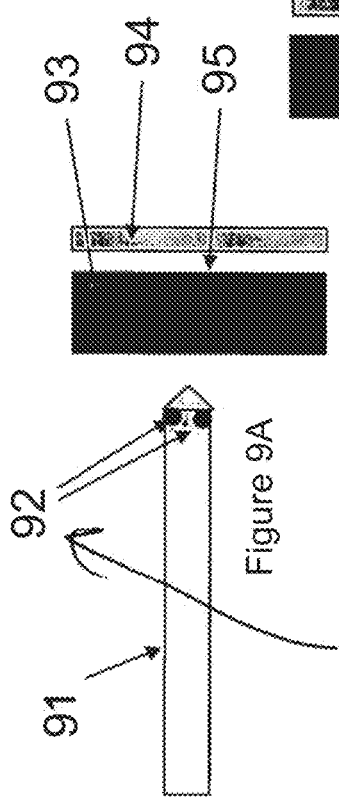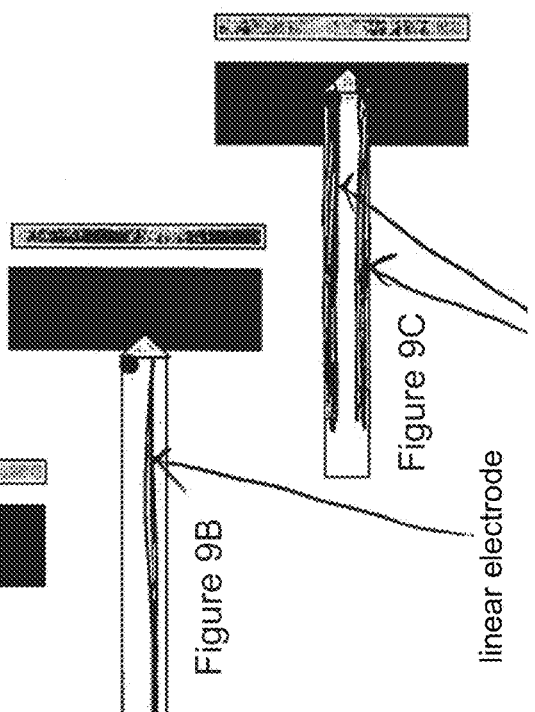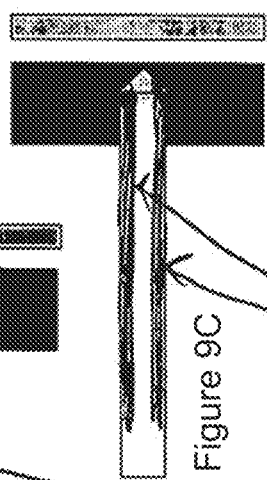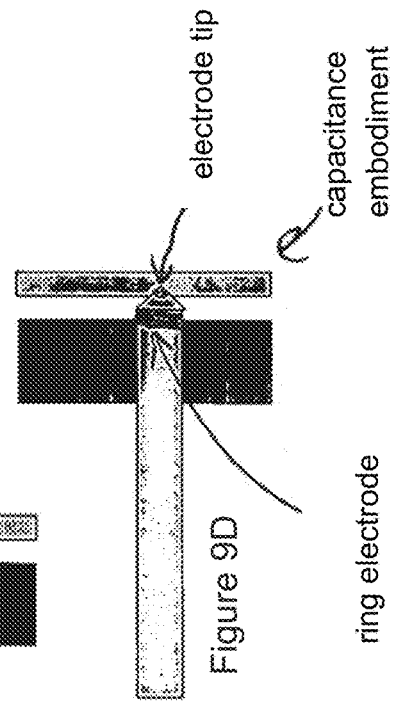

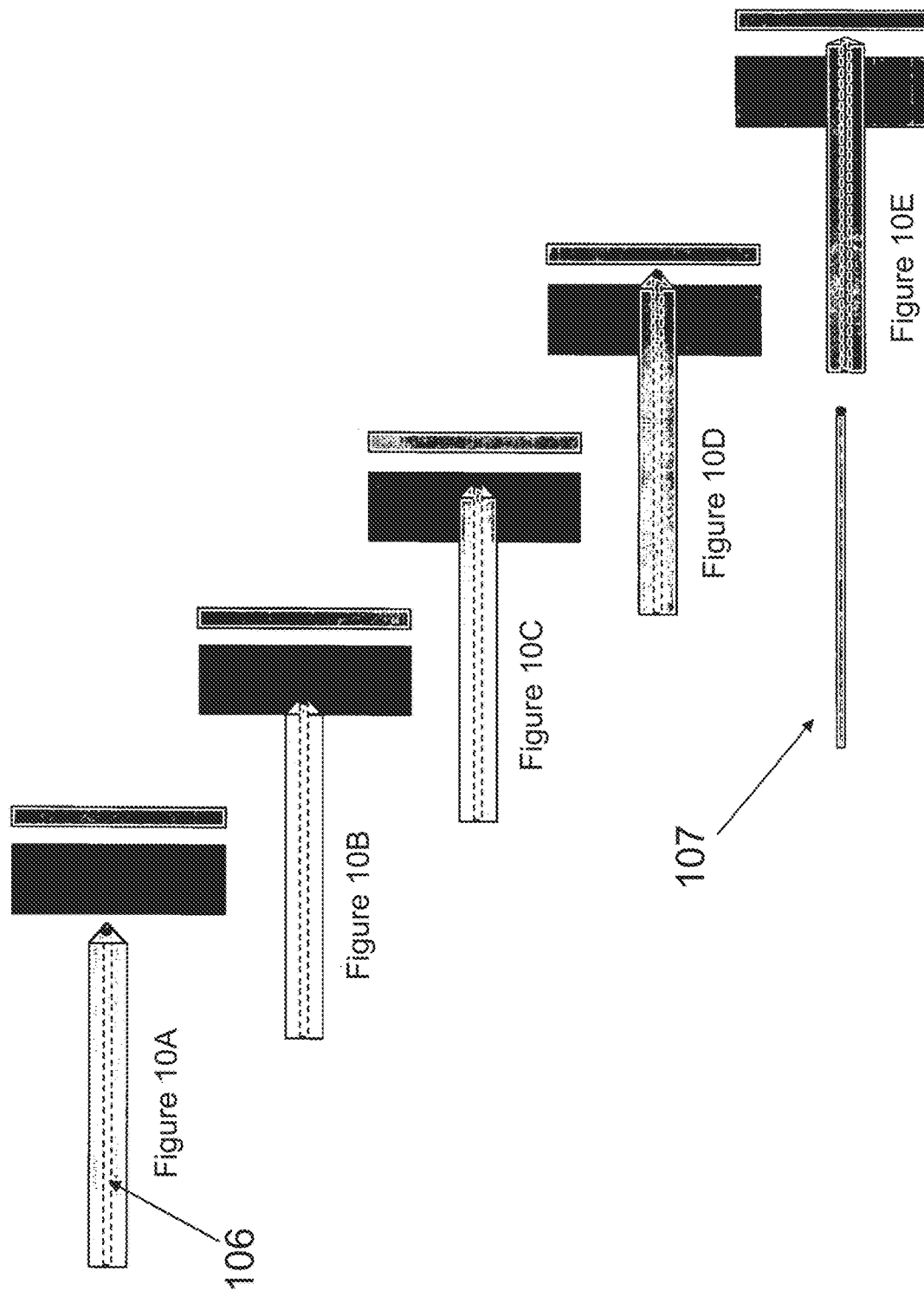

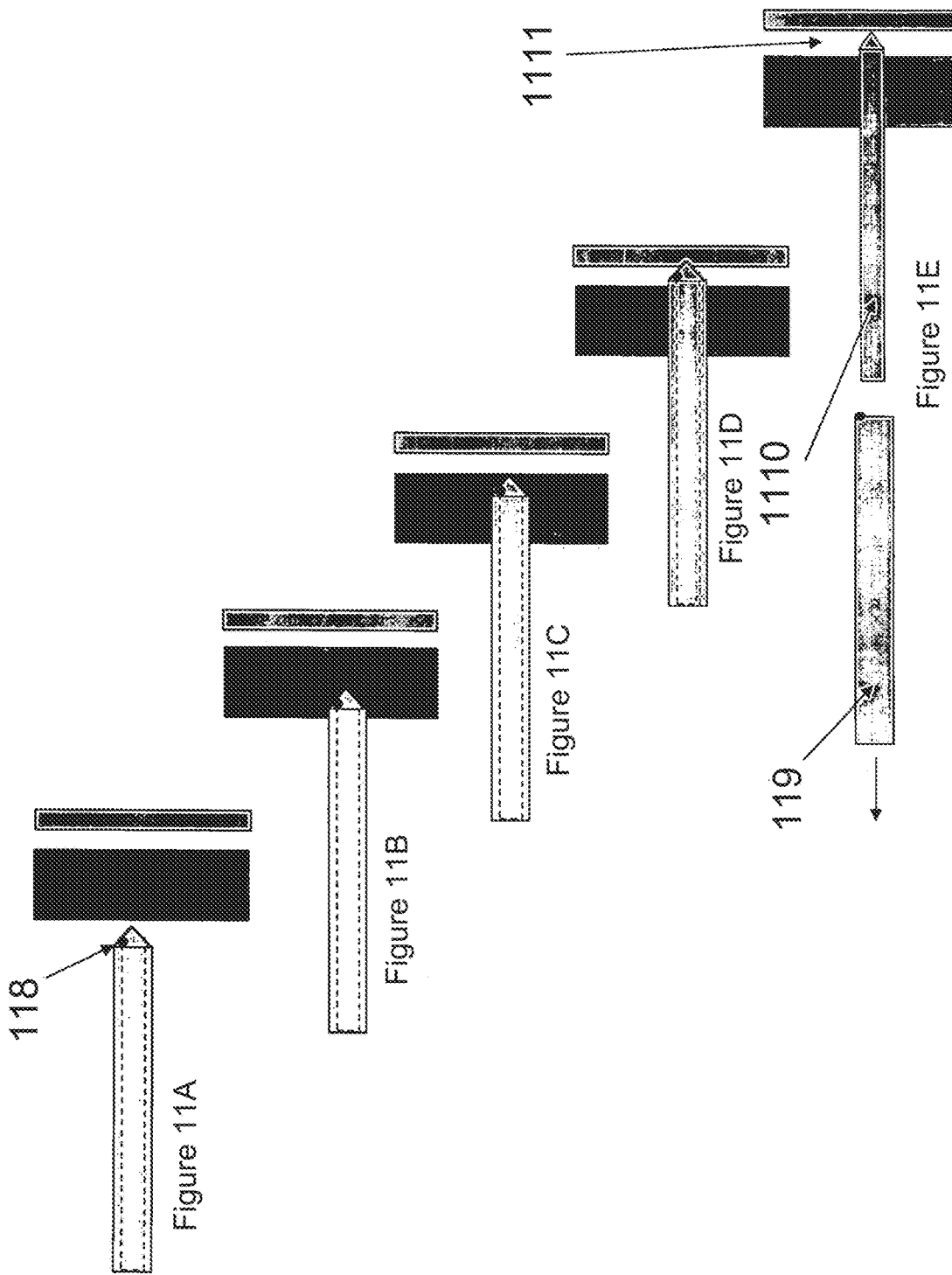

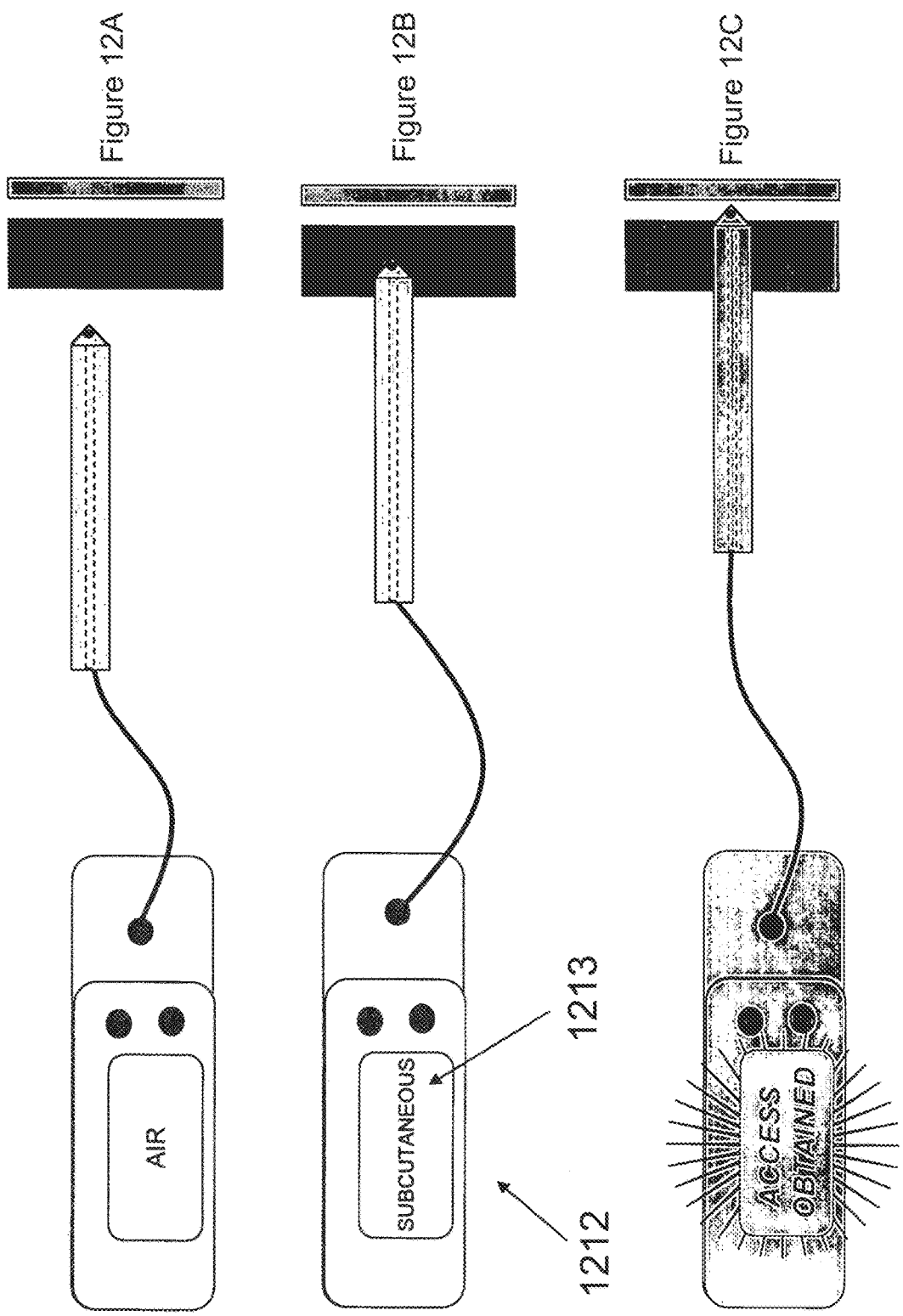

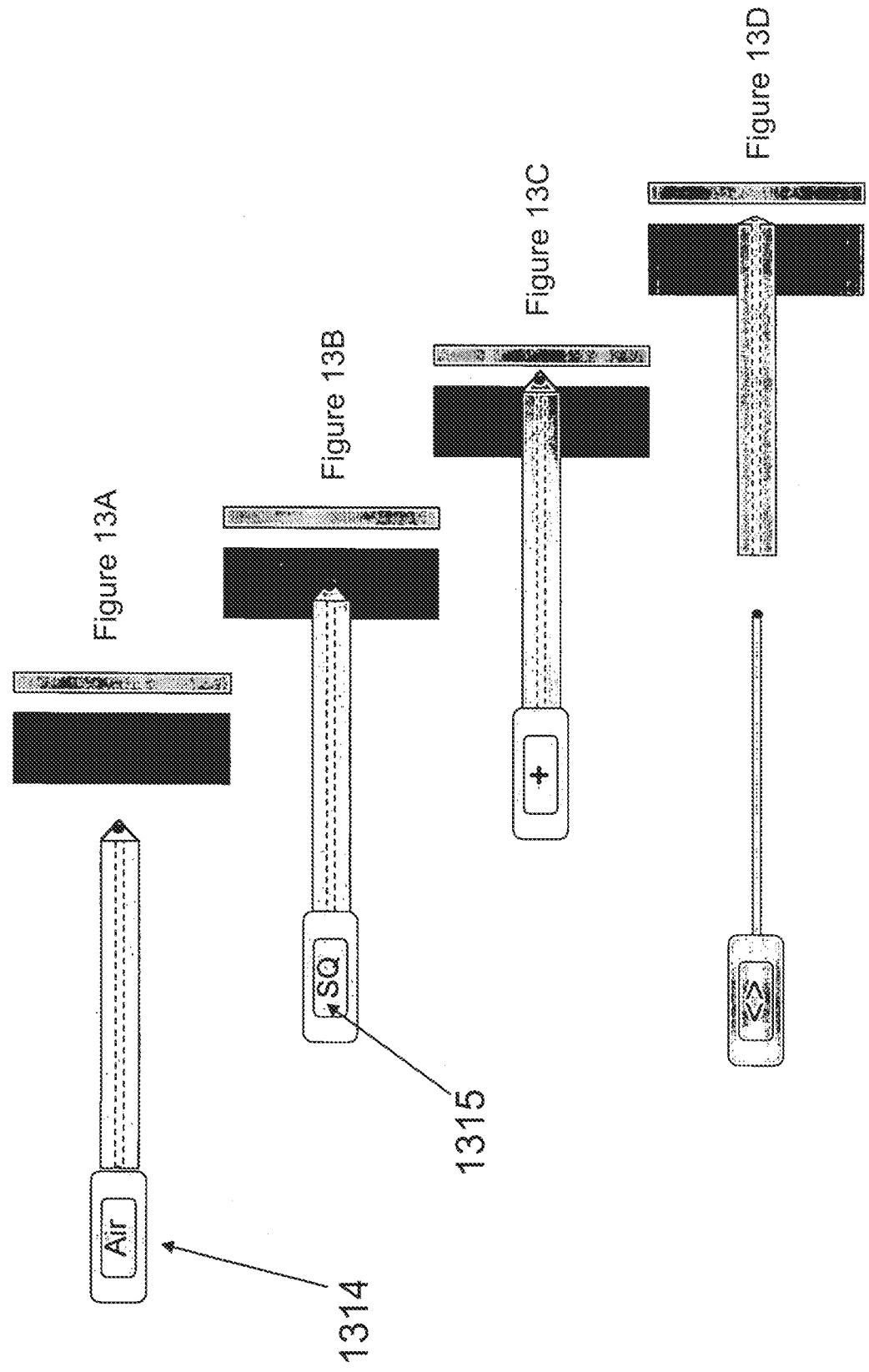

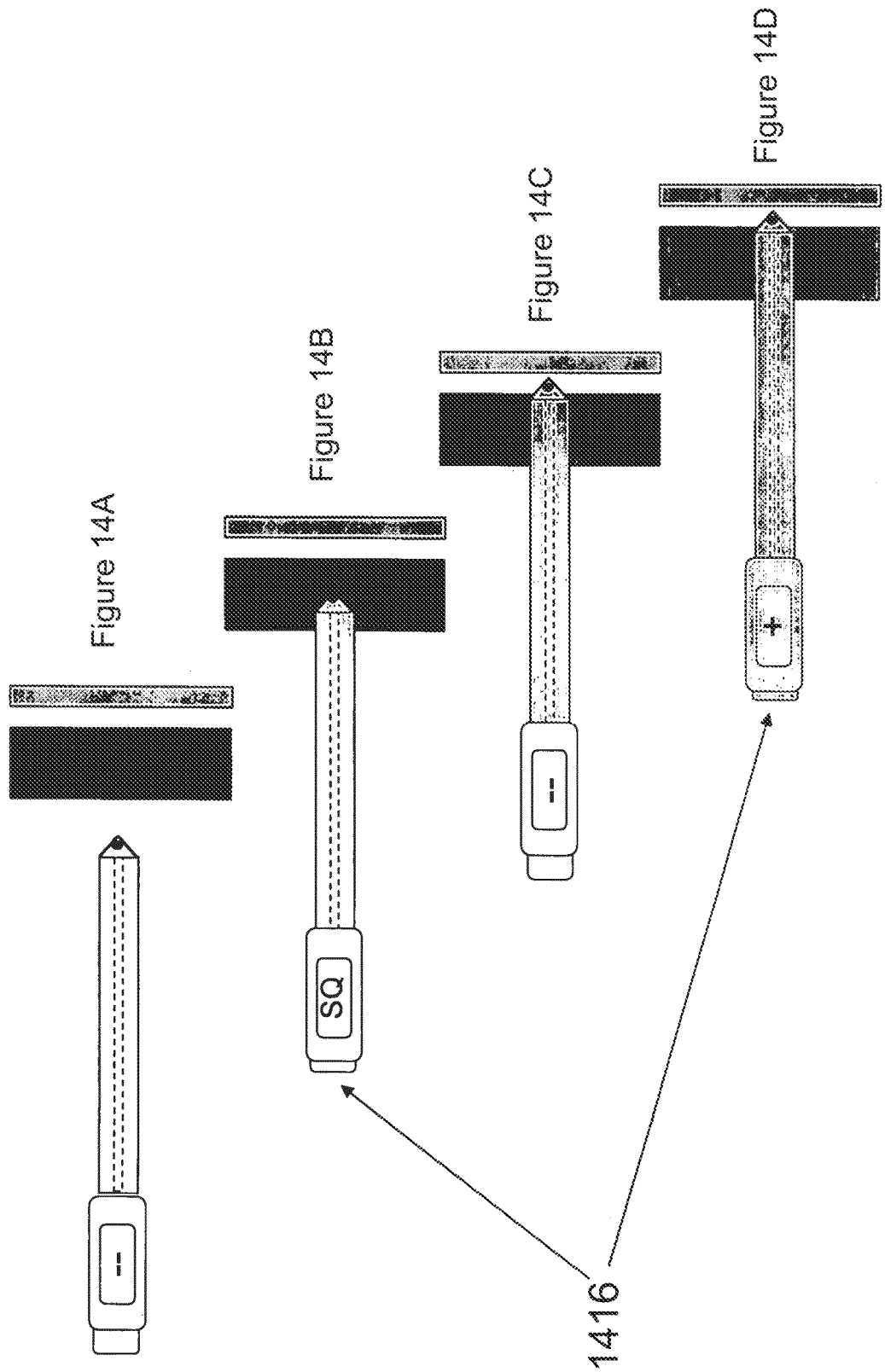

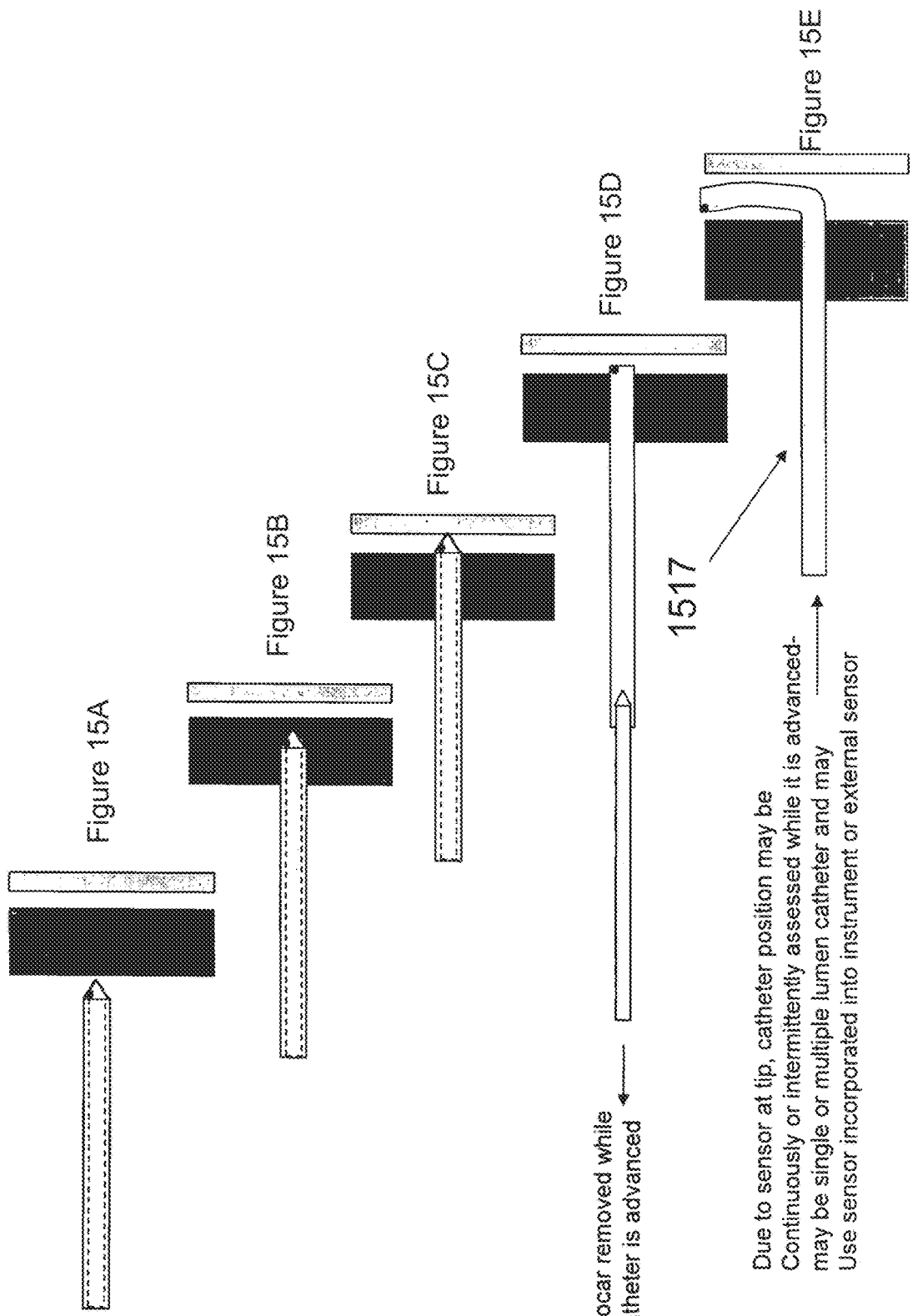

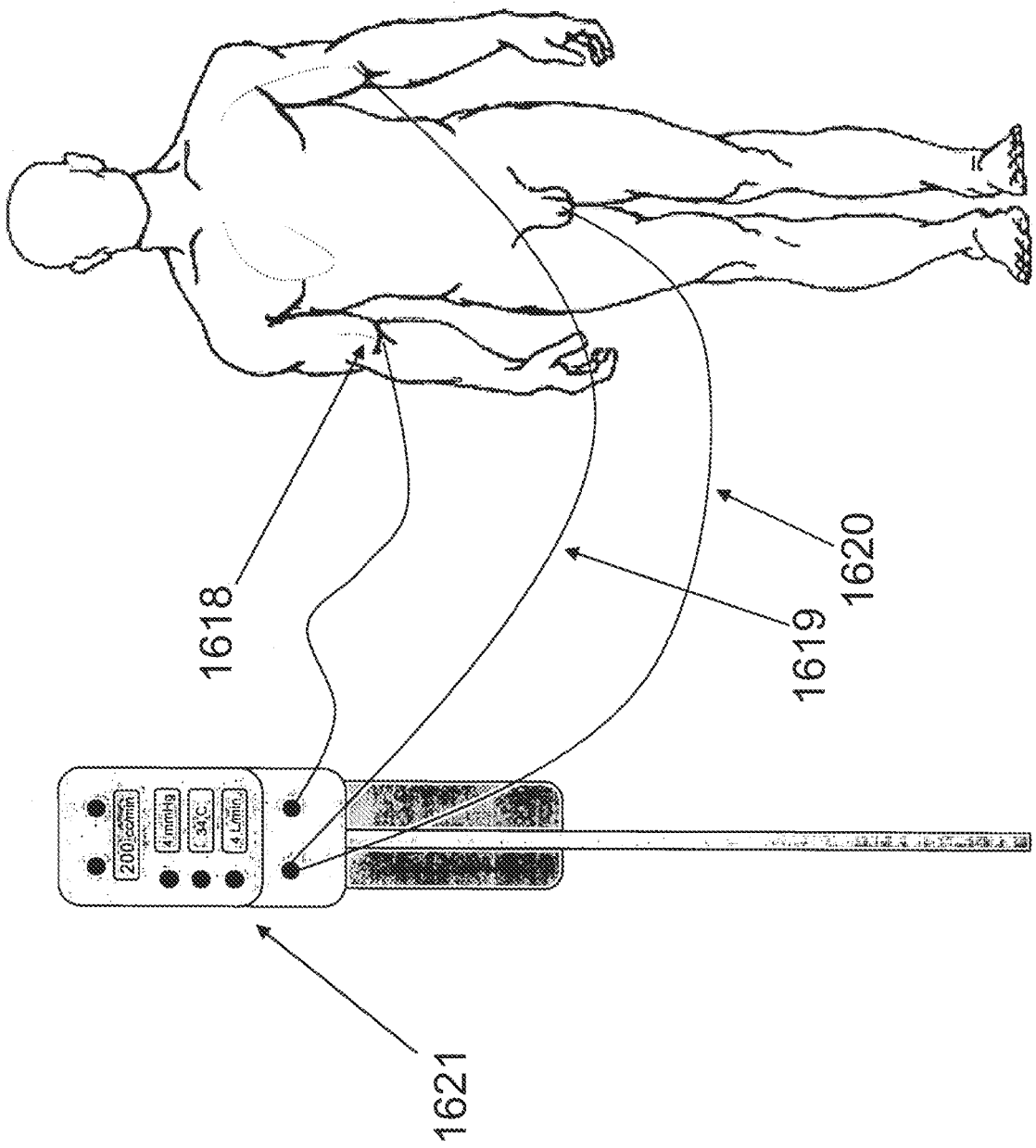

DEVICE AND METHOD FOR SAFE ACCESS AND AUTOMATED THERAPY

CROSS-REFERENCE TO RELATED APPLICATIONS

This application is continuation of U.S. application Ser. No. 15/013,813, filed Feb. 2, 2016, which is a continuation of U.S. application Ser. No. 13/937,102, filed Jul. 8, 2013; which application is a continuation of U.S. application Ser. No. 13/354,210, filed Jan. 19, 2012, now U.S. Pat. No. 8,480,648; which application is a continuation of U.S. application Ser. No. 12/098,365, filed Apr. 4, 2008, now U.S. Pat. No. 8,100,880; which application claims the benefit of U.S. Provisional Patent Application No. 60/921,974, filed Apr. 5, 2007 to Burnett, entitled "Safety Access Device, Fluid Output Monitor & Peritoneal Organ Preservation", all disclosures of which are incorporated by reference herein in their entirety.

FIELD OF THE INVENTION

The present invention relates to the field of medical devices, in particular devices capable safely accessing bodily spaces or cavities.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Fluids and other substances are infused into patients for a variety of reasons. For example, fluids may be given to a patient intravenously to hydrate the patient or to control overall blood volume.

It is often important to control infusion of fluid into patients in order to optimize the therapy being provided. Monitoring of patient parameters can consume precious health care time and resources, however. Fluid infusion into patients is therefore not always optimized.

Mantle US 2006/0161107 describes a system that extracts fluid from a body cavity, processes the fluid and then recirculates fluid back into the cavity. Mantle does not describe infusion of a fluid into a patient without extraction of the fluid from the patient, however. In addition, the parameters on which the Mantle system is controlled are limited.

SUMMARY OF THE INVENTION

One aspect of the invention provides an automated therapy system having an infusion catheter; a sensor adapted to sense a patient parameter; and a controller communicating with the sensor and programmed to control flow output from the infusion catheter into a patient based on the patient parameter without removing fluid from the patient. In some embodiments, the sensor may be incorporated into the catheter, and in other embodiments, the sensor may be separate from the catheter. The sensor may be, e.g., an ECG sensor; an EEG sensor; a pulse oximetry sensor; a blood pressure sensor; a cardiac output sensor; a thermodilution cardiac output sensor; a cardiac stroke volume sensor; a heart rate sensor; a blood flow sensor; a pH sensor; a blood $pO_2$ sensor; an intracranial pressure sensor; and/or a solute sensor.

In embodiments of the invention, the catheter may be a peripheral venous catheter; a central venous catheter; an arterial catheter; or a peritoneal catheter (possibly incorporating an intraperitoneal pressure sensor).

Another aspect of the invention provides a method of controlling infusion of a fluid to a patient. The method includes the following steps: monitoring a patient parameter with a sensor to generate a sensor signal; providing the sensor signal to a controller; and adjusting fluid flow to the patient based on the sensor signal without removing fluid from the patient. In some embodiments, the method includes the step of monitoring cardiac output with the sensor and, possibly, adjusting fluid flow to the patient based on cardiac output monitored by the sensor. In embodiments of the invention, the patient parameter includes an electrocardiogram; an electroencephalogram; blood oxygen saturation; blood pressure; cardiac output; cardiac stroke volume; heart rate; blood flow; total circulating blood volume; whole body oxygen consumption; pH; blood $pO_2$; osmolarity; peritoneal cavity compliance; intrathoracic pressure; bladder pressure; and/or rectal pressure.

In some embodiments, the adjusting step includes the step of adjusting fluid flow to achieve or maintain patient euvolumia; adjusting flow of a therapeutic agent (such as a chilled medium) to the patient; adjusting fluid flow to the patient through a peripheral venous catheter; adjusting fluid flow to the patient through a central venous catheter; adjusting fluid flow to the patient through an arterial catheter; and/or adjusting fluid flow to the patient's peritoneal cavity.

Yet another aspect of the invention provides a method of treating hypotension in a patient. The method includes the following steps: monitoring a patient parameter (such as blood pressure or cardiac output) with a sensor to generate a sensor signal; providing the sensor signal to a controller; and adjusting fluid flow to the patient based on the sensor signal without removing fluid from the patient.

Still another aspect of the invention provides a method of treating sepsis in a patient. The method includes the following steps: monitoring a patient parameter (such as blood pressure, central venous pressure, or cardiac output) with a sensor to generate a sensor signal; providing the sensor signal to a controller; and adjusting fluid flow to the patient based on the sensor signal without removing fluid from the patient. Prevention of hypotension and/or hypovolemia is critical in the care of patients that have suffered severe hemorrhage or are septic. These patients are very difficult to monitor and treat, taking significant nursing time and still resulting in suboptimal therapy due to the intermittent nature of the blood pressure, central venous pressure and/or cardiac output checks. The present invention, then, will optimize fluid flow to the patient while also freeing up the already over-taxed nursing staff for other duties.

Yet another aspect of the invention provides a method of inducing and reversing therapeutic hypothermia in a patient. The method includes the steps of: monitoring intracranial pressure to generate a sensor signal; providing the sensor signal to a controller; and adjusting rate of hypothermia induction or rewarming based on intracranial pressure (such as by adjusting fluid flow to the patient), or depth of hypothermia, based on the sensor signal.

In some embodiments of the invention, irrigation and/or lavage of bodily tissues, cavities or spaces (or other patient interventions) may be optimized using a sensor or sensors to report electrical, chemical, acoustic, mechanical properties, pressure, temperature, pH or other parameters surrounding the access device in order to automate and optimize the irrigation/lavage.

Embodiments of the invention include a peritoneal catheter containing one or more sensors which may detect changes in electrocardiograph monitoring, electroencephalograph monitoring, pulse oximetry (either internally or peripherally), peritoneal cavity compliance, intrathoracic pressure, intraperitoneal pressure, intraperitoneal pressure waveforms, bladder pressure, rectal pressure, cardiac output, cardiac stroke volume, cardiac rate, blood flow (e.g., in superior mesenteric, celiac, renal or other arteries), pressure in veins (particularly the inferior vena cava or those that empty into the inferior vena cava, e.g., femoral vein), pressure in arteries (particularly those distal to the aorta, e.g., the femoral artery), total circulating blood volume, blood oxygenation (e.g., in rectal mucosa, peripheral fingers and toes, etc.), whole body oxygen consumption, pH and/or arterial $pO_2$ (or any other parameter that shows a measurable change with increased peritoneal pressure) to ensure safety of automated or manual peritoneal lavage. The invention also includes methods of performing peritoneal lavage using such devices.

Embodiments of the invention include an intravascular catheter containing one or more sensors which may detect changes in electrocardiograph monitoring, electroencephalograph monitoring, pulse oximetry (either internally or peripherally), partial pressure of oxygen or $CO_2$, pH, temperature, blood pressure, central venous pressure, cardiac output, cardiac stroke volume, cardiac rate, blood flow (e.g., in superior mesenteric, celiac, renal or other arteries), total circulating blood volume, pressure in veins (particularly those that empty into the inferior vena cava, e.g., femoral vein), pressure in arteries (particularly those distal to the aorta, e.g., the femoral artery), blood oxygenation (e.g., in rectal mucosa, peripheral fingers and toes, etc.), whole body oxygen consumption, pH and/or arterial $pO_2$ (or any other parameter that shows a measurable change with intravascular volume overload) to ensure safety of manual or automated intravascular infusion. The invention also includes methods of using such devices.

Other embodiments of the invention include control of the rate of infusion to minimize negative effects observed by the sensors. The invention may be used to induce and/or maintain hypothermia or hyperthermia; maximize hydration and/or intravascular volume in a patient receiving intravenous fluids (such as, e.g., post-operative patients, post-hemorrhage patients, septic patients or other intensive care patients).

Disclosed is a method and device for detection of intake and/or output in an individual. Fluid detection may be fully automated and the user may be alerted if volumes become too low or too high. The data may also be automatically routed to a centralized data collection server so that it may be collected and accessed without the requirement for nursing or other healthcare personnel to record the information manually. The output receptacle, in particular, may contain wireless technology, ie RFID, as well to optimize data collection and reduce nursing burden.

In reviewing the obstacles of urine output monitoring and data collection, then, it becomes clear that what is needed for widespread adoption is an easily implemented system capable of accurately measuring urine output wherein the use of the device reduces the nursing burden while reporting any issues with urine output in a timely manner. The present invention may also measure and report bladder temperature in real-time and this information may be used to alert the healthcare providers of changes in therapy and/or may be used to control and direct depth of therapeutic hypothermia. The reservoir/receptacle may also contain sensors capable of detecting other materials of interest within the fluid including, but not limited to: hemoglobin, blood, bacteria, leukocyte esterase, glucose, protein, particulate matter, etc. This information may also trigger an alert to provide real-time data monitoring of these parameters. Additionally, the present invention anticipates the use of wired or, ideally, wireless transmission of data to allow for centralized collection of data and centralized reporting. This is, once again, useful in reducing healthcare provider burden by allowing fewer personnel to monitor the data from all of the patients utilizing said system.

In addition, the system of the present invention anticipates the use of RFID technology within or attached to the reservoir itself which may be remotely queried and interrogated by one or more RFID readers. The data collected may be encrypted and specific to each receptacle such that the up.ne output reported may be securely associated with an individual patient. In its optimal embodiment, the reservoir may contain conducting channels connected to the RFID circuitry which determine the urine level by detection of the level of a simple short-circuit through the conducting fluid itself which may then be reported by the RFID chip to the reader. This cheap, easy-to-use system overcomes the obstacles of previous attempts to automate urine output monitoring.

In addition, information collected using the present invention may be used to automatically adjust therapeutic hypothermia, delivery of medicine or other interventions.

Disclosed is a method and device for safe access of a bodily tissues, spaces or cavities and automated therapy. The improved safety of the current invention is based, in part, on the ability of the access system to report entrance into the tissue/space/cavity via an integrated sensor. In its preferred embodiment, additional sensing capabilities may be incorporated, as well, to optimize the automated therapy delivered or intervention required.

In reviewing the obstacles of providing safe access to bodily cavities and spaces, it becomes clear that over- and under-insertion of invasive instrumentation is a major issue. During catheter placement in major vessels, for example, many of the complications that occur are due to over-insertion of the insertion needle or sliding of the catheter over the needle at a point when the needle is not appropriately positioned. The disclosed invention, then, is a method and device for safe access of a bodily tissues, spaces or cavities. The improved safety of the current invention is based, in part, on the ability of the access system to report entrance into the tissue, space, or cavity via a sensor integrated within, or inserted simultaneously with, the instrument itself. In its preferred embodiment, additional sensing capabilities may be incorporated, as well, to optimize the desired intervention or therapy to be delivered.

1) A device for accessing bodily tissues, spaces or cavities outside of the respiratory tree wherein; said access device or its insertion instrumentation incorporates a sensor and wherein said sensor may report access to the desired tissues, spaces or cavities.

2) The device of 1 wherein said sensor is capable of sensing optical, electrical, chemical, acoustic and/or mechanical properties to differentiate between tissues, spaces or cavities and indicate when said device is in the desired location.

3) The device of 1 wherein said access device may incorporate additional sensors in order to optimize therapy provided by said device.

4) The device of 2 wherein said access device sensor may report entrance into a cavity and wherein said additional sensor (or sensors) may report pressure, temperature, pH or other parameters in order to optimize therapy.

5) The device of 2 wherein said cavity to be accessed may be the peritoneal cavity, and wherein said sensor may directly or indirectly detect entry into this cavity.

6) The device of 4 wherein said additional sensors may directly or indirectly detect mechanical properties (such as pressure), chemical composition, thermal properties, electrical properties, acoustic properties or optical•properties to optimize filling of the peritoneal cavity with gases, liquids and/or solids.

7) The device of 2 wherein said cavity to be accessed may include peritoneal, pleural, cerebrospinal, biliary, gastrointestinal, gastric, intestinal, urinary cavities, or pathologic tissues, and wherein said sensor may directly or indirectly detect entry into this cavity.

8) The device of 2 wherein said space to be accessed may include the cardiovascular, venous, arterial, lymphatic, ureteral cerebrospinal ventricular spaces, or pathologic spaces and wherein said sensor may directly or indirectly detect entry into this space.

9) The device of 2 wherein said tissues to be accessed may include lung, liver, heart, bladder, brain, intestinal, pancreatic, splenic, vascular tissues, or pathologic spaces and wherein said sensor may directly or indirectly detect entry into these tissues.

10) The device of 1 wherein said sensor is incorporated into the device itself.

11) The device of 1 wherein said sensor is incorporated into the instrumentation required to insert said access device.

12) The device of 1 wherein said sensor may be introduced along with said access device and may be reversibly attached or contained within said device.

13) The device of 1 wherein said sensor may be physically connected to an external display.

14) The device of 1 wherein said sensor may be wirelessly connected to an external display.

15) The device of 13 wherein said display may be incorporated into said access device.

16) The device of 13 wherein said display may be reversibly or irreversibly attached to an external display.

17) The device of 14 wherein said display may be incorporated into said access device 18) The device of 1 wherein said sensor may be intermittently activated to detect the tissues surrounding the sensor.

19) The device of 18 wherein said sensor may be repeatedly activated to detect the tissues surrounding the sensor.

20) The device of 1 wherein said sensor continuously detects which tissues surround the sensor.

21) The device of 2 wherein said sensor detects optical transfer of wavelengths from a transmitter to a, receiver and wherein the wavelength conduction path includes the sensor incorporated within said device.

22) The device of 2 wherein said sensor detects electrical properties surrounding said sensor to detect unique electrical signatures of the surrounding tissues.

23) The device of 2 wherein said sensor detects chemical properties (ie albumin, pH, etc.) surrounding said sensor to detect unique chemical components, or concentrations of components, within the tissues/spaces.

24) The device of 2 wherein said sensor detects acoustic properties of the surrounding tissues/spaces to detect entrance into the desired tissue/space.

25) The device of 2 wherein said sensor detects mechanical properties (such as pressure, shear forces, etc.) surrounding said sensor to detect entrance into desired tissue/space.

26) The device of 2 wherein multiple sensors of any type are used to indicate exact positioning and the composition of the fluid surrounding said device.

27) The device of 26 wherein one or more sensors positively predict tissue/space access while one or more sensors negatively predict tissue/space access.

28) The device of 26 wherein one or more sensors positively predict tissue/space access while one or more sensors detect potential complicating factors, ie the presence of unexpected blood, etc.

29) The device of 3 wherein irrigation and/or lavage of bodily tissues, cavities or spaces is optimized by said additional sensors and wherein said access device contains a sensor to detect pressure, temperature, or other parameters to optimize the irrigation/lavage.

30) A method for accessing bodily tissues, spaces or cavities wherein; an access device or its insertion instrumentation incorporates a sensor and wherein said sensor may report access to the desired tissues, spaces or cavities.

31) The method of 30 wherein said sensor is capable of sensing optical, electrical, chemical, acoustic and/or mechanical properties to differentiate between tissues, spaces or cavities and indicate when said device is in the desired location.

32) The method of 30 wherein said access device may incorporate additional sensors in order to optimize therapy provided by said device.

33) The method of 31 wherein said access device sensor may report entrance into a cavity and wherein said additional sensor (or sensors) may report electrical, chemical, acoustic, mechanical properties, pressure, temperature, pH or other parameters in order to optimize therapy.

34) The method of 31 wherein said cavity to be accessed may be the peritoneal cavity, and wherein said sensor may directly or indirectly detect entry into this cavity 35) The method of 33 wherein said additional sensors may directly or indirectly detect mechanical properties (such as pressure), chemical composition, electrical properties, acoustic properties or optical properties to optimize filling of the peritoneal cavity with gases, liquids and/or solids.

36) The method of 31 wherein said cavity to be accessed may include peritoneal, pleural, cerebrospinal, biliary, gastrointestinal, gastric, intestinal, urinary cavities, or pathologic spaces and wherein said sensor may directly or indirectly detect entry into one or more of these cavities.

37) The method of 31 wherein said space to be accessed may include the cardiovascular, venous, arterial, lymphatic, ureteral cerebrospinal ventricular spaces, or pathologic spaces and wherein said sensor may directly or indirectly detect entry into one or more of these spaces.

38) The method of 31 wherein said tissues to be accessed may include lung, liver, heart, bladder, brain, intestinal, pancreatic, splenic, vascular tissues, or pathologic spaces and wherein said sensor may directly or indirectly detect entry into one or more of these tissues.

39) The method of 30 wherein said sensor is incorporated into the device itself.

40) The method of 30 wherein said sensor is incorporated into the instrumentation required to insert said access device.

41) The method of 30 wherein said sensor may be introduced along with said access device and may be reversibly attached or contained within said device.

42) The method of 30 wherein said sensor may be physically connected to an external display.
43) The method of 30 wherein said sensor may be wirelessly an external display.
44) The method of 42 wherein said display may be incorporated into said access device.
45) The method of 42 wherein said display may be reversibly or irreversibly attached to an external display.
46) The method of 43 wherein said display may be incorporated into said access device.
47) The method of 30 wherein said sensor may be intermittently activated to detect the tissues surrounding the sensor.
48) The method of 47 wherein said sensor may be repeatedly activated to detect the tissues surrounding the sensor.
49) The method of 30 wherein said sensor continuously detects which tissues surround the sensor.
50) The method of 31 wherein said sensor may detect optical transfer of wavelengths from a transmitter to a receiver and wherein the location of said device may be determined based on absorption or transmission of said wavelengths.
51) The method of 31 wherein said sensor detects electrical properties surrounding said sensor to detect and report unique electrical signatures of the surrounding tissues and allow for avoidance of undesirable tissues/spaces including conductance, impedance, resistance, capacitance, etc.
52) The method of 31 wherein said sensor detects chemical properties (ie albumin, pH, etc.) surrounding said sensor to detect unique chemical components, or concentrations of components, within the tissues/spaces and avoidance of undesirable tissues/spaces.
53) The method of 31 wherein said sensor detects acoustic properties of the surrounding tissues/spaces to detect entrance into the desired tissue/space and/or avoidance of undesirable tissues/spaces.
54) The method of 31 wherein said sensor detects mechanical properties (such as pressure, shear forces, etc.) surrounding said sensor to detect entrance into desired tissue/space and/or avoidance of undesirable tissues/spaces.
55) The method of 31 wherein said sensor detects thermal properties of the surrounding tissues/spaces to detect entrance into the desired tissue/space and/or avoidance of undesirable tissues/spaces.
55) The method of 31 wherein multiple sensors of any type may be used to indicate exact positioning and the composition of the fluid surrounding said device.
56) The method of 55 wherein one or more sensors may be used to positively predict tissue/space access while one or more sensors negatively predict tissue/space access.
57) The method of 55 wherein one or more sensors may be used to positively predict tissue/space access while one or more sensors detect potential complicating factors, ie the presence of unexpected blood, etc.
58) The method of 55 Wherein one or more sensors may be used to provide multiple data points to help determine the exact position of said sensor or sensors.
59) The method of 32 wherein irrigation and/or lavage of bodily tissues, cavities or spaces may be optimized by said additional sensors and wherein said access device contains a sensor or sensors to report electrical, chemical, acoustic, mechanical properties, pressure, temperature, pH or other parameters surrounding the access device in order to optimize said irrigation/lavage.
59) The method of 32 wherein an intervention performed in said tissues, cavities or spaces may be optimized by said additional sensors and wherein said access device contains a sensor or sensors to report electrical, chemical, acoustic, mechanical properties, pressure, temperature, pH or other parameters surrounding the access device in order to optimize said intervention.
60) A peritoneal catheter containing one or more sensors which may detect changes in electrocardiograph monitoring, electroencephalograph monitoring, pulse oximetry (either internally or peripherally), peritoneal cavity compliance, intrathoracic pressure, intraperitoneal pressure, bladder pressure, rectal pressure, cardiac output, cardiac stroke volume, cardiac rate, blood flow (i.e. in superior mesenteric, celiac, renal or either arteries), pressure in veins (particularly those that empty into the IVC, i.e. femoral vein), pressure in arteries (particularly those distal to the aorta, i.e. the femoral artery), blood oxygenation (i.e. in rectal mucosa, peripheral fingers and toes, etc.), whole body oxygen consumption, pH and/or arterial pO2 (or any other parameter that shows a measurable change with increased peritoneal pressure) to ensure safety of automated or manual peritoneal lavage.
61) A method of performing peritoneal lavage wherein changes in electrocardiograph monitoring, electroencephalograph monitoring, pulse oximetry (either internally or peripherally), peritoneal cavity compliance, intrathoracic pressure, intraperitoneal pressure, bladder pressure, rectal pressure, cardiac output, cardiac stroke volume, cardiac rate, blood flow (i.e. in superior mesenteric, celiac, renal or other arteries), pressure in veins (particularly those that empty into the IVC, i.e. femoral vein), pressure in arteries (particularly those distal to the aorta, i.e. the femoral artery), blood oxygenation (i.e. in rectal mucosa, peripheral fingers and toes, etc.), whole body oxygen consumption, pH and/or arterial pO2 (or any other parameter that shows a measurable change with increased peritoneal pressure) are monitored and may be utilized to ensure safety of automated or manual peritoneal lavage.
62) An intravascular catheter containing one or more sensors which may detect changes in electrocardiograph monitoring, electroencephalograph monitoring, pulse oximetry (either internally or peripherally), partial pressure of oxygen or CO2, pH, temperature, blood pressure, central venous pressure, cardiac output, cardiac stroke volume, cardiac rate, blood flow (i.e. in superior mesenteric, celiac, renal or other arteries), total circulating blood volume, pressure in veins (particularly those that empty into the IVC, i.e. femoral vein), pressure in arteries (particularly those distal to the aorta, i.e. the femoral artery), blood oxygenation (i.e. in rectal mucosa, peripheral fingers and toes, etc.), whole body oxygen consumption, pH and/or arterial pO2 (or any other parameter that shows a measurable change with intravascular volume overload) to ensure safety of manual or automated intravascular infusion.
63) A method of performing intravascular infusion wherein one or more sensors may detect changes in electrocardiograph monitoring, electroencephalograph monitoring, pulse oximetry (either internally or peripherally), partial pressure of oxygen or CO2, pH, temperature, blood pressure, central venous pressure, cardiac output, cardiac stroke volume, cardiac rate, blood flow (i.e. in superior mesenteric, celiac, renal or other arteries), total circulating blood volume, pressure in veins (particularly those that empty into the IVC, i.e. femoral vein), pressure in arteries (particularly those distal to the aorta, i.e. the femoral artery), blood oxygenation (i.e. in rectal mucosa, peripheral fingers and toes, etc.), whole body oxygen consumption, pH and/or arterial pO2 (or arty other parameter that shows a measurable change with intravascular volume overload) which may be used to regulate the rate of infusion.

64) The method of 63 wherein said rate of infusion may be maximized in the absence of negative effects to the monitored parameters.
65) The method of 63 wherein said rate of infusion may be reduced or halted in the presence of negative effects to the monitored parameters.
66) The method of 63 wherein said intravascular infusion may be utilized to induce and/or maintain hypothermia or hyperthermia.
67) The method of 63 wherein said intravascular infusion may be utilized to optimize hydration and/or intravascular volume in any patient receiving intravenous fluids.
68) The method of 63 wherein said intravascular infusion may be utilized to optimize hydration and/or intravascular volume in post-operative patients.
69) The method of 63 wherein said intravascular infusion may be utilized to optimize hydration and/or intravascular volume in septic or other intensive care patients.
70) The method of 63 wherein said intravascular infusion may be utilized to optimize hydration and/or intravascular volume with additional inputs which may include sensor-based urine output detection.
71) The method of 70 wherein said monitored parameters and urine output information may be used, according to a hydration algorithm, to report issues with intake or output and automatically correct these issues via automated changes to the rate of infusion and/or addition of diuretics.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-9D—Side view of the sensor incorporated into the instrument.

FIGS. 10A-10E—Side view of the sensor incorporated into removable insertion trocar.

FIGS. 11A-11E—Side view of the sensor Incorporated into removable sheath.

FIGS. 12A-12C—Side view of the External Reader attached to Access Device.

FIGS. 13A-13D—Side view of the continuous reader incorporated into Access Device (trocar embodiment).

FIGS. 14A-14D—Side view of the intermittent reader incorporated into Access Device (trocar embodiment).

FIGS. 15A-15E—Side view of the sensor incorporated into access device (shown as catheter with insertion trocar).

FIG. 16—Intravenous fluid flow automated by sensors.

DETAILED DESCRIPTION OF THE INVENTION

Figure 1:
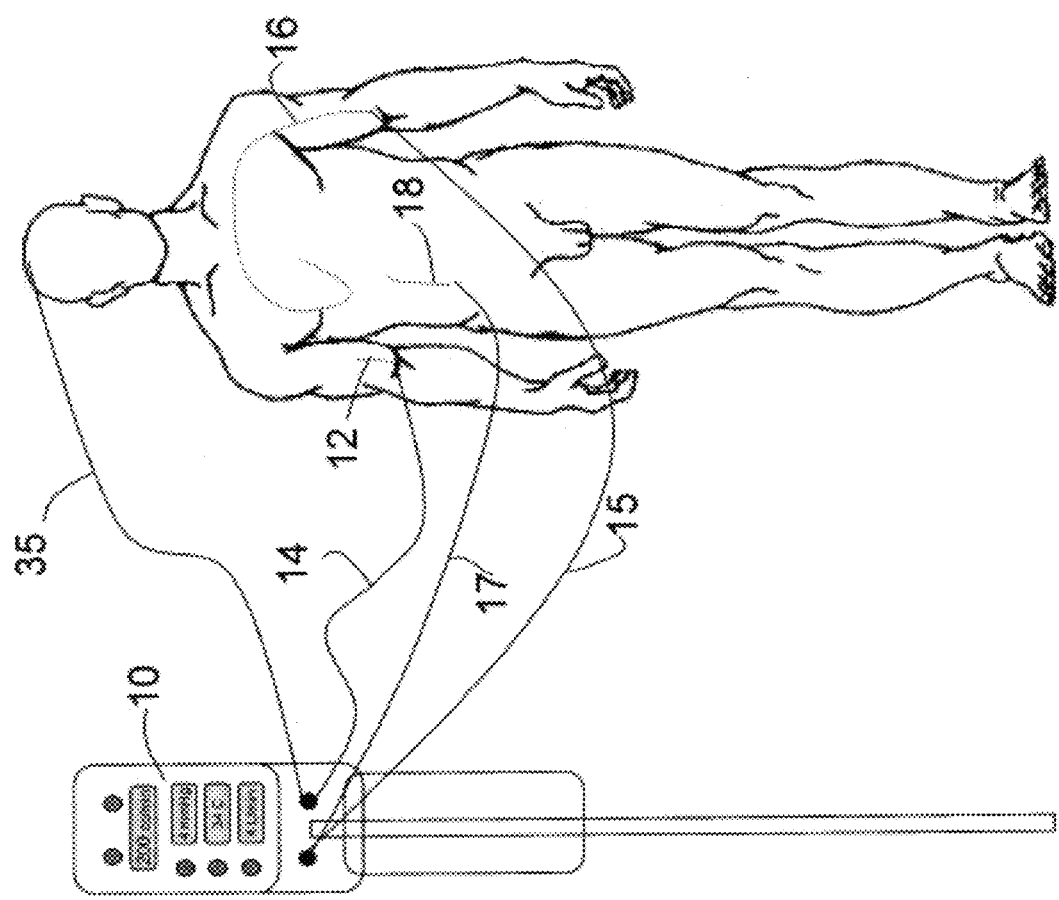
FIG. 1 shows an automated infusion system in which infusion is controlled based on patient parameters sensed by multiple sensors.
Figure 2:
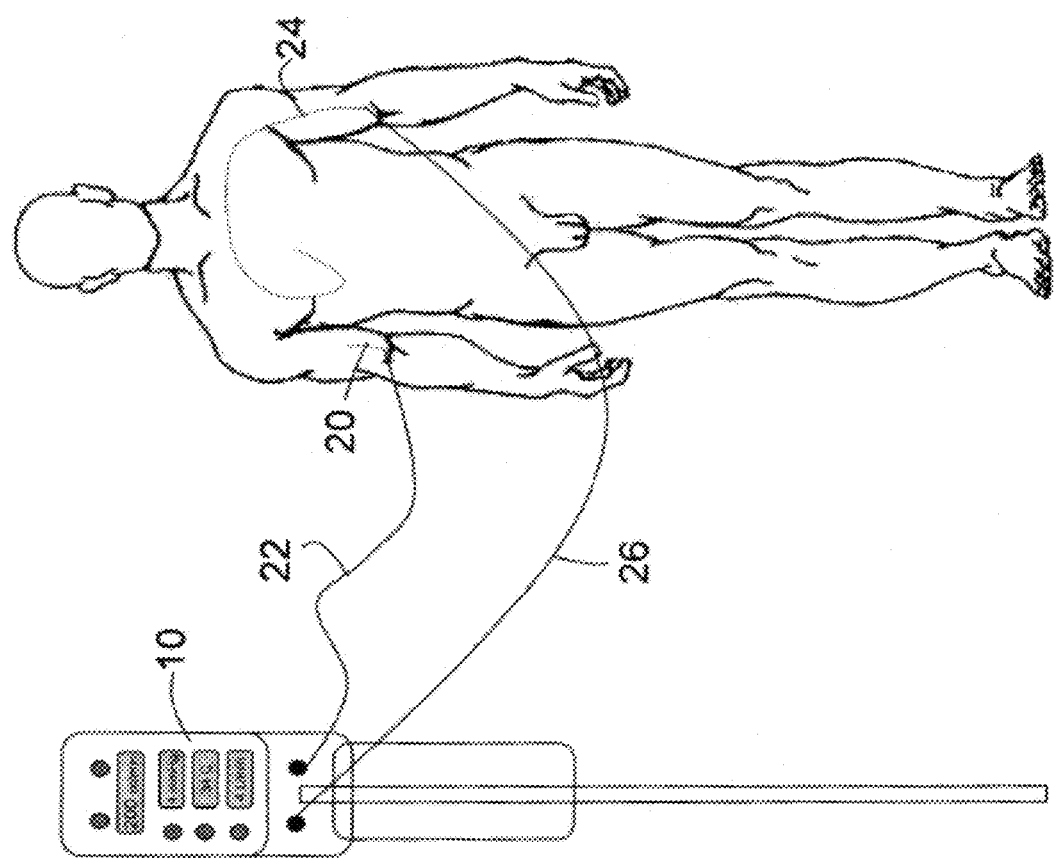
FIG. 2 shows an automated infusion system in which a sensor controlling infusion is separate from the infusion catheter.
Figure 3:
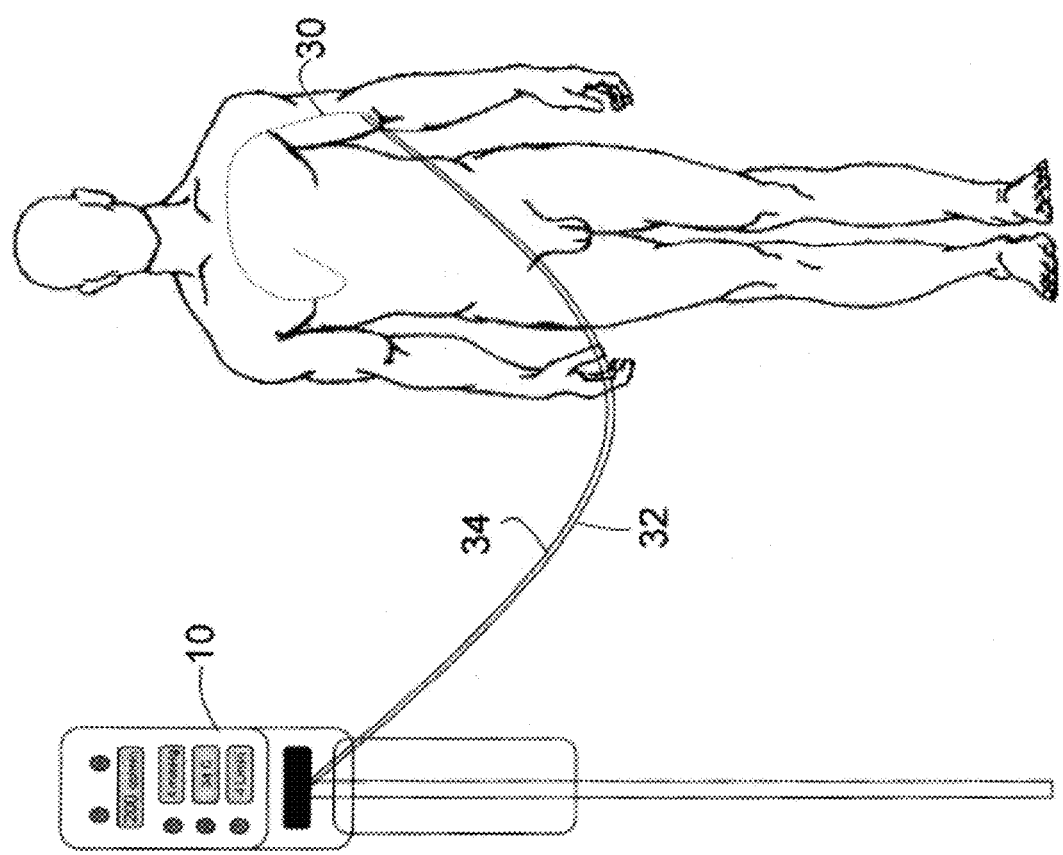
FIG. 3 shows an automated infusion system in which sensing and infusion are performed with the same catheter.

FIGS. 1-3 show embodiments of the invention wherein intravenous fluid delivery may be automated, or manually adjusted, based on feedback from one or more sensors. In these embodiments, the infusion catheter may have a sensor to aid in insertion, but this is not necessary for this invention.

In one embodiment, the infusion catheter also is used to detect the parameters used to optimize therapy. FIG. 1 shows an infusion system with an infusion controller 10 operably connected to an intravenous infusion catheter 12 via an infusion line 14. Infusion catheter 12 also has a sensor (not shown) attached to or associated with it to monitor a patient parameter. The sensor also communicates with controller 10 either through line 14 or via some other communication channel. Suitable patient parameters include electrocardiograph monitoring, electroencephalograph monitoring, pulse oximetry (either internally or peripherally), blood pressure, central venous pressure, cardiac output, cardiac stroke volume, cardiac rate, blood flow (e.g., in superior mesenteric, celiac, renal or other arteries), total circulating blood volume, pressure in veins (particularly those that empty into the inferior vena cava, e.g., femoral vein), pressure in arteries (particularly those distal to the aorta, e.g., the femoral artery), blood oxygenation (e.g., in rectal mucosa, peripheral fingers and toes, etc.), whole body oxygen consumption, pH, arterial $pO_2$, or any other parameter that shows a measurable change with intravascular volume overload.

As shown in FIG. 1, additional catheters, here envisioned as a peripherally inserted central catheter (PICC) 16 and/or a peritoneal catheter 18, or additional sensors on infusion catheter 12 may be used to monitor these or other parameters, and to optimize the infusion rate and achieve euvolemia without fluid overload or dehydration. Flow of fluid and/or a fluid/solid mixture (e.g., an ice slurry) to catheters 16 and/or 18 is controlled by controller 10 through lines 14, 15 and/or 17, respectively. The information from the sensors may then be transmitted to central controller 10, which integrates all of this information to determine the flow of intravenous fluid through catheter 12 and/or catheter 16 and flow of peritoneal fluid through catheter 18. This information may be used to achieve or maintain euvolemia (e.g., in sepsis, hemorrhagic shock, etc.) or to maximize infusion for delivery of a therapeutic agent, e.g., chilled fluid and/or solids to achieve hypothermia. Alternatively, catheters 16 and 18 may be used with sensors to obtain patent information, and fluid may be infused into the patient solely through catheter 16 or catheter 18. In yet further embodiments, the depth of hypothermia and/or rate of hypothermia induction or rewarming may be tailored based on intracranial pressure sensor(s) (not shown) communicating with controller 10 via communication line 35. This system and method may be used with any method of inducing hypothermia (e.g., cooling blankets, intravascular catheters, intravenous fluid infusion, peritoneal lavage, etc.) so long as the change in temperature, particularly rewarming, is controlled at least in part by an intracranial pressure sensor.

The sensor or sensors, whether cables/catheters or percutaneous monitoring technologies, and whether wired or wireless, may also be separate from the infusion line so long as the information from this sensor or sensors is transferred to the control unit in order to optimize fluid flow. Thus, as shown in FIG. 2, the patient parameter sensor may be associated with PICC 24 and communicate with controller via line 26, and infusion to the patient may be via line 22 and infusion catheter 20, as controlled by controller 10. In some embodiments, of course, sensing and infusion may be performed through a single catheter, such as PICC 30, and controlled by controller 10 through lines 32 and 34, as shown in FIG. 3. In some embodiments, the infusion and monitoring device of the current invention may incorporate an access sensor, such as that described in a commonly owned patent application, U.S. patent application Ser. No. 12/098,355, filed Apr. 4, 2008, titled "Device And Method For Safe Access To A Body Cavity".

One example of such a device is a peripheral venous, central venous or arterial catheter that is capable of maintaining hydration without causing fluid overload. The catheter may incorporate a sensor that may detect central venous pressure, total circulating blood volume, peripheral venous pressure, cardiac output or osmolarity, and/or solute concentrations (e.g., chloride, sodium, etc.) in order to prevent fluid overload. The sensor may also be external to the catheter, so long as the output of said sensor is capable of controlling fluid flow through the catheter. In this embodiment, fluid flow is controlled by the output of the sensor, which is integrated by a fluid flow control unit which alters the rate of fluid flow based on this output. This embodiment may allow the user to bolus large volumes of fluids or solids into the vascular space in order to rehydrate, induce hypothermia or reverse hypothermia, or deliver a therapeutic agent or maintain blood pressure in sepsis.

In addition, this technology may provide a fully automated mechanism to optimize fluid flow into the vessel without fluid overloading the patient. Without this automated fluid delivery coupled to hemodynamic parameter monitoring, the patient is in danger of dehydration or fluid overload from infusion of fluid into any body cavity. This technology may also be applied to liquid or solid infusion into any body cavity or space in so long as the fluid flow is automated based on feedback from sensors within the body (possibly incorporated into the catheter itself) in order to optimize the volume of infusion.

This device and method of automating fluid flow based on hemodynamic sensor-based feedback may also be used to generate intravenous hypothermia. In its current state, IV hypothermia induction is limited due to concerns of fluid overload. If the hemodynamic parameters of the patient can be measured and fluid flow directly or indirectly controlled based on the output of these measurements, the volume of fluid can be maximized while ensuring hemodynamic instability. In this embodiment, the sensor may be incorporated within the catheter, and fluid flow into the vasculature may be tailored based on central venous pressure, total circulating blood volume, peripheral venous pressure, cardiac output or osmolarity, and/or solute concentrations (e.g., chloride, sodium, etc.) in order to prevent fluid overload.

In one embodiment, the fluid infusion catheter also may function as a thermodilution cardiac output sensor such that the same fluid that is used to generate hypothermia may also be used to detect cardiac output. This information may then be relayed, either directly or indirectly, back to the fluid infusion controller to increase, decrease or even halt fluid flow based on these parameters. For example, if cardiac output is low and venous pressure or total circulating volume is low, the patient has a low circulating volume and large volumes of fluid may be safely delivered. If the cardiac output is normal, fluid may also be safely delivered, but the cardiac output must be monitored to ensure that it does not begin to decrease (an indication of fluid overload). Blood flow, as detected by, for instance, thermodilution may be determined in a peripheral vessel as well. These data, while relatively useless on their own in a clinical setting due to variability in peripheral blood flow, may provide a baseline flow profile which may be rechecked over time in order to compare flow within that individual vessel to the baseline flow. Relatively improved flow may be correlated to improved cardiac output, while a relative reduction in flow may be correlated to fluid overload.

This same system may be used to infuse normal fluids or hypothermic fluids to sepsis patients or patients requiring intensive maintenance of their hemodynamic status. Sepsis patients that are aggressively monitored do much better than those that are not. Aggressive monitoring is very nurse-intensive, however. A system that provides automated optimal fluid infusion based on sensed parameters to ensure that fluid overload does not occur and that fluid infusion is not insufficient would be an improvement over current methods of treating sepsis patients. The devices and methods for automated sensor-based input to control fluid flow to a patient may be applicable to a wide range of conditions and should not be limited to the narrow scope of the conditions requiring fluid infusion described here.

The logic controller of the present invention may provide improved safety by monitoring for any of the deleterious changes expected with excess fluid flow, e.g., into the peritoneal cavity or vascular space. Examples of monitored parameters that may signal a warning or automatically result in an adjustment to rate of fluid infusion/extraction and/or fluid temperature include: electrocardiograph monitoring, electroencephalograph monitoring, pulse oximetry (either internally or peripherally), peritoneal cavity compliance, intrathoracic pressure, intraperitoneal pressure, intraperitoneal pressure waveforms, bladder pressure, rectal pressure, cardiac output, cardiac stroke volume, cardiac rate, total circulating blood volume, blood flow (e.g., in superior mesenteric, celiac, renal or other arteries), pressure in veins (particularly those that empty into the IVC, e.g., femoral vein), pressure in arteries (particularly those distal to the aorta, e.g., the femoral artery), blood oxygenation (e.g., in rectal mucosa, peripheral fingers and toes, etc.), whole body oxygen consumption, pH and arterial $pO_2$ and any other parameter that shows a measurable change once the peritoneal or vascular spaces have been overloaded.

These parameters in particular have been found to change with increases in peritoneal pressure, with significantly negative impact on each parameter found at 40 mmHg. Thus, monitoring for these changes in conjunction with a peritoneal infusion catheter of the present invention will allow for even greater safety with peritoneal infusion. These parameters may be measured a variety of ways and the data transmitted either wirelessly or via wires to the logic controller in order to alert the healthcare provider or to automatically adjust the fluid flow/temperature in order to optimize both the flow of the peritoneal fluid and patient safety.

Figure 4:
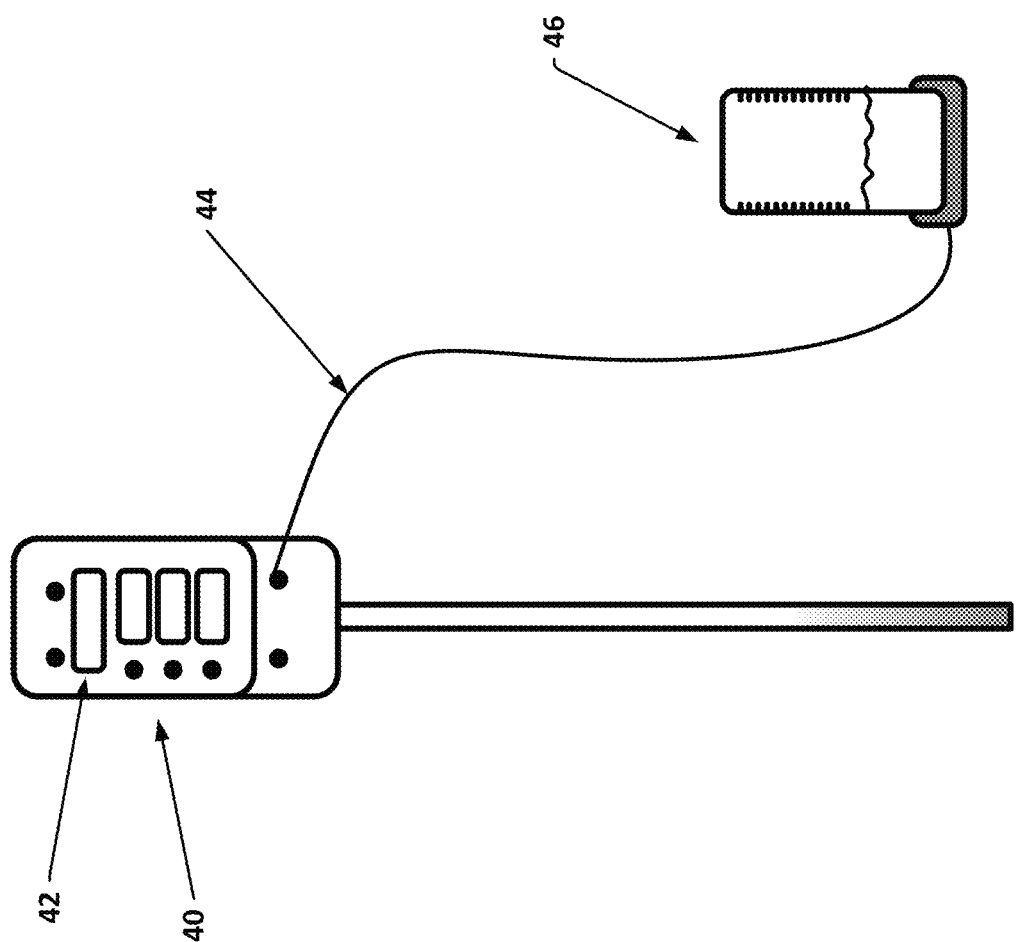
FIG. 4—Console with optional sensor lead (may be wireless).

FIG. 4 illustrates a console 40 with optional sensor lead 44 which may or may not be wireless. The console itself may record output/input data 42. This data may be held in memory, printed or directly transmitted to a centralized data collection server. Said console may connect to the urine receptacle 46 to determine urine output either via a wire or wirelessly.

Figure 5:
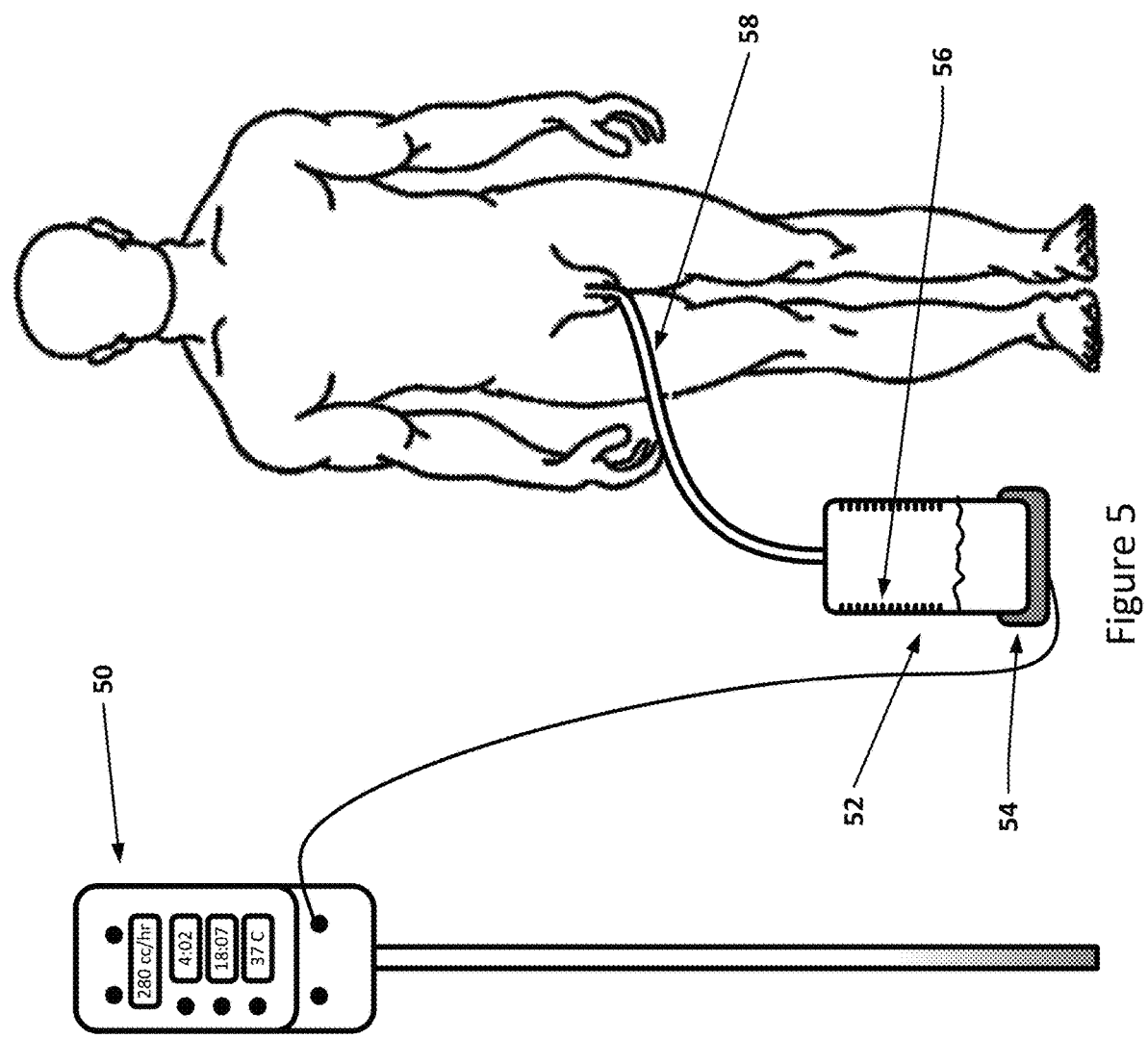
FIG. 5—Sensor-based Urine Output Measurement.

FIG. 5 illustrates sensor-based Urine Output Measurement. In this instance, the console 50 or RFID reader can trigger alert if urine output is too low or too high over a set period of time. May also have intravenous infusion capabilities to provide input and output data and tailor delivery of fluids and/or medicines (ie diuretics) via an automated system based on the urine output feedback. The device may include an optional Docking Station 54—ideally reusable, may connect to receptacle 52 and transmit data to control unit either via wires or, ideally, wirelessly. May also measure urine level via weight, etc. Optional Urine Level Sensors 56 may report level of urine via conductivity, resistance, impedance, etc. Sensors may also continuously or intermittently detect bacteria, hemoglobin or other substances of interest in urine. Urinary catheter 58 is also shown.

Figure 6:
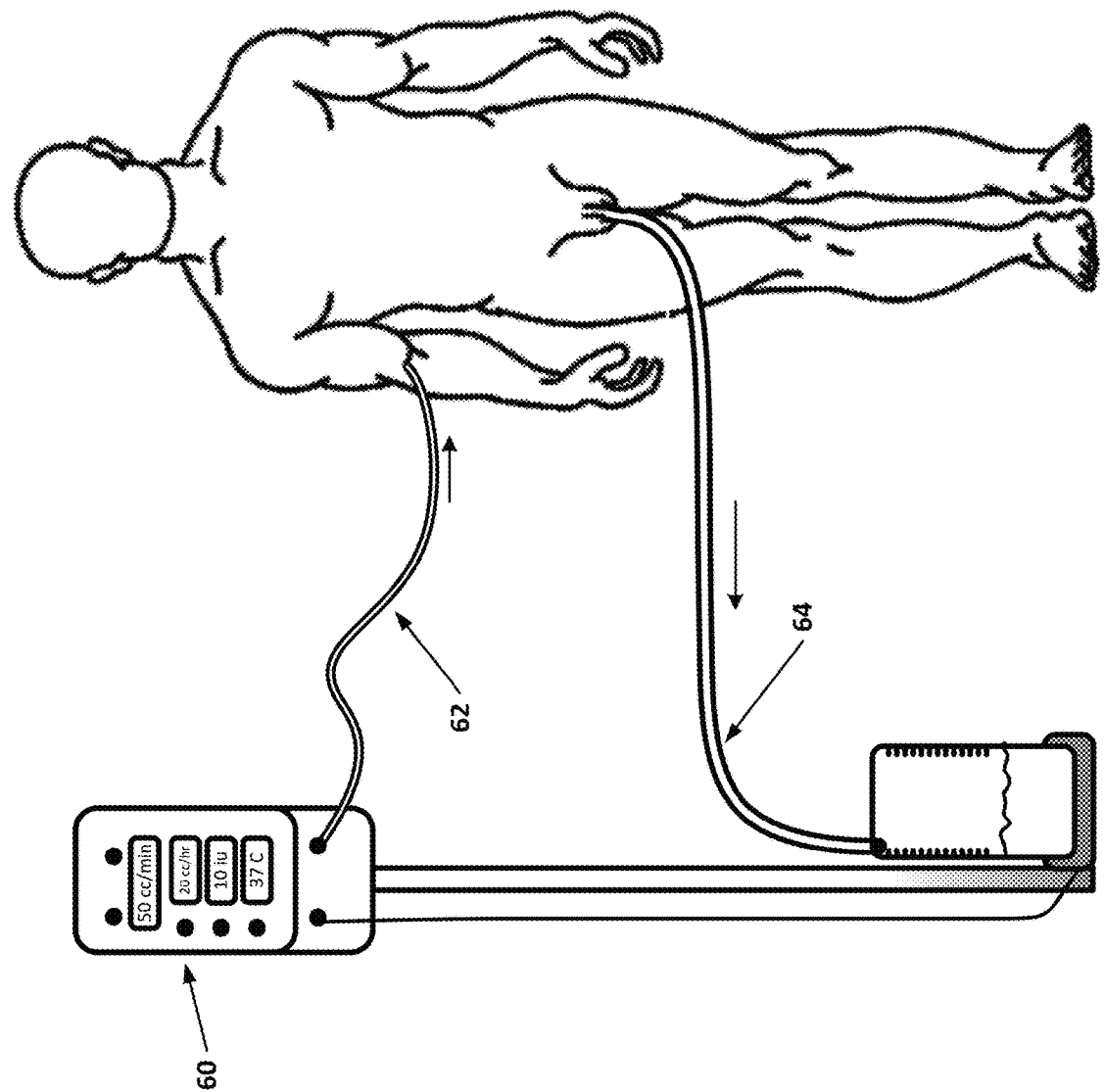
FIG. 6—Console with automated infusion therapy system.

FIG. 6 illustrates a console 60 with automated infusion therapy system. Console may integrate patient data, ie fluids received, urine output recorded, etc. to automate therapy, ie delivery of fluids or LASIX if the pt is dehydrated or fluid overloaded respectively. May also trigger local alert (ie beeping) and centralized alert (ie system alarm) if urine output drops too low. The console may also integrate a fluid infusion or medicine infusion capabilities, ie an IV infusion pump, and may adjust infusion rates based on this data or data acquired from other sensors in an automated fashion. The console may communicate wirelessly, as well, to these and any other sensors within the body. Infusion catheter 62 is also shown—may deliver drugs or fluid based on urine output and other parameters. Urinary catheter 64 is also shown.

Figure 7:
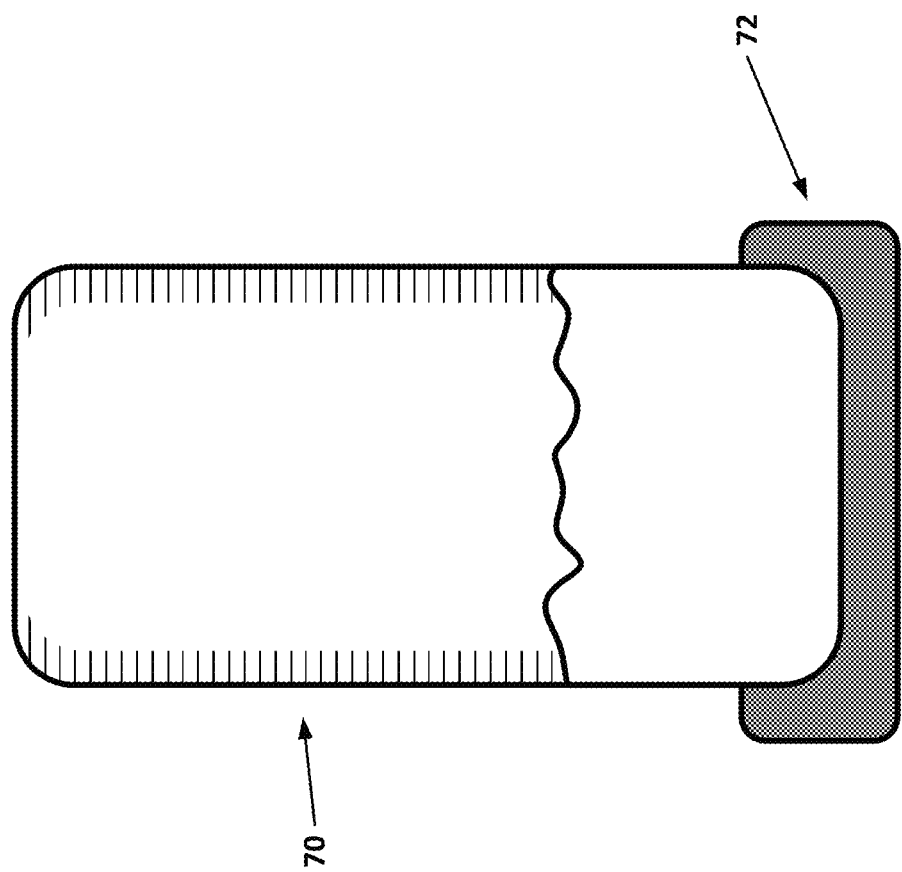
FIG. 7—Volume-sensing Urine Receptacle with Dock.

FIG. 7 illustrates a volume-sensing Urine Receptacle with reusable communicating and/or sensing element. The receptacle 70 itself may detect urine output based upon level at which sensors are triggered—ie have hash-marks represent electrical contacts and when an electrical path is made between two contacts, and all contacts below, the level can be reported at that level. May be electrical, optical, chemical or mechanical sensors. May also contain diffuse or discrete sensing areas that may detect the presence of absence of certain materials of interest, ie hemoglobin, protein, glucose, bacteria, blood, leukocyte esterase, etc. either intermittently or continuously. May report any and/or all of this information to the console, locally (via beeping, etc.) or centrally via piping data to a central information collection area. Alerts triggered if urine output drops below 30 cc/hr in post-operative setting or any otherwise defined threshold. May also be disposable and connect to the docking station 72 which may communicate the data from said, receptacle wirelessly. The docking station may be connected anywhere on said receptacle, or optionally, not included at all. If a docking station is used, it may detect urine output based simply upon weight or pressure applied to base. May contain disposable or, ideally, durable optical, electrical or chemical sensors capable of sensing glucose, electrolytes, bacteria, hemoglobin, blood, etc. May interface with specifically designed area of the urine receptacle to allow for this measurement—ie an optically clear window for optical measurement of blood, etc. May also fasten onto the urine receptacle in any position so long as it engages the receptacle. This or the receptacle itself may contain an inductive antenna and/or RFID capabilities to allow for wireless querying and reporting of the level of urine or other fluid collection.

Figure 8:
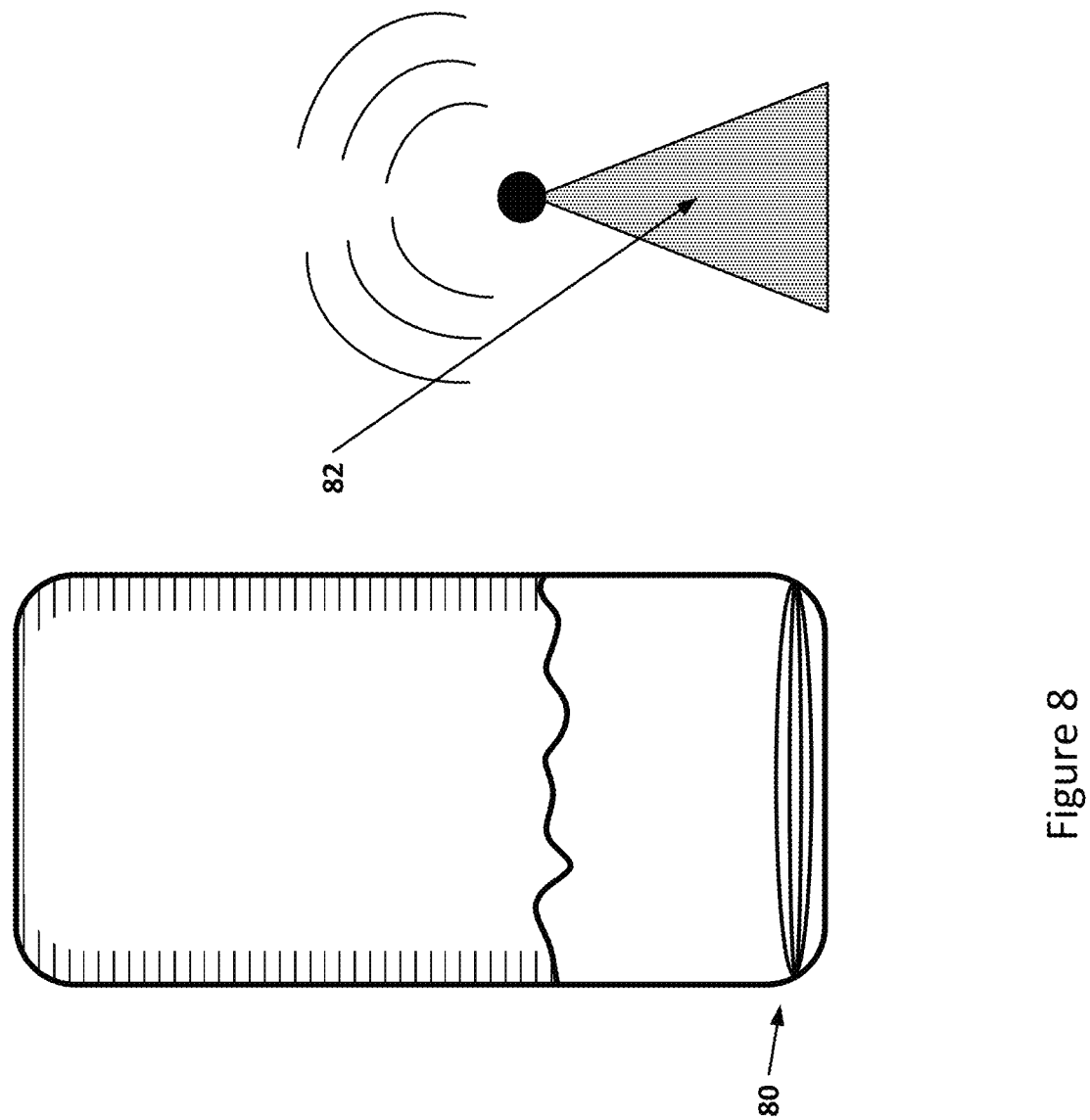
FIG. 8—Volume-sensing Urine Receptacle—RFID Embodiment.

FIG. 8 illustrates a volume-sensing Urine Receptacle 80 with RFID capabilities. This embodiment may contain RFID circuitry to collect and transmit data directly from within the receptacle to a RFID Reader. When queried by the RFID reader may simply detect impedance, resistance, capacitance or any other electrical or nonelectrical property to detect the urine level and report this back to the reader. Reader may then trigger alert if urine output is high or low. The RFID chip may be capable of detecting changes in optical, chemical, electrical, acoustic or mechanical properties, as well. May be active or passive RFID and may contain antenna in any position and, ideally, may transmit a unique signal to identify the receptacle to the reader and allow multiple receptacles to be queried at once. The RFID chip may incorporate a small battery (to extend its range) in an active RFID embodiment or may be passive in nature and be powered solely by the transmissions from said RFID reader. The RFID Reader 82 may query device from a distance to wirelessly check the urine output level or may be centralized to query all receptacles within a unit, floor or hospital and issue an alert if urine output drops too low (or is too high). May record urine output, as well, and replace the individual unit consoles illustrated in FIGS. 1-3. The RFID reader may also report data from other sensors within said system, including bladder temperature or presence of certain materials within the urine, ie blood, hemoglobin, leukocyte esterase, other indicators of bacterial infection, protein, glucose, etc.

In another embodiment, a urinary catheter capable of sensing physiologic parameters is envisioned. Additional sensing capabilities may include: blood pressure, oxygen saturation, pulse oximetry, heart rate, EKG, capillary fill pressure, etc. In particular, the incorporation of pulse oximetry technology to allow for blood oxygen concentration or saturation determination with a urinary catheter is envisioned. This device may function by incorporating pulse oximetry capabilities anywhere along the length of the catheter, but ideally the sensor or sensors will be contained within the tubing of the device to ensure approximation to the urethral mucosa. With this invention, the healthcare provider will be able to decompress the bladder with a urinary catheter and obtain pulse oximetry data in a repeatable and accurate manner. The power source for this device may be incorporated within the urinary drainage bag or within the catheter itself. Ideally, the pulse oximeter will be reusable and the catheter interface will be disposable wherein the pulse oximeter is simply reversibly attached to the disposable catheter and removed once measurements of oxygen are no longer desired. The urinary catheter, then, may contain an optically transparent, or sufficiently transparent, channel for the oximetry signal, ie a fiber-optic cable, transparent window, etc., and an interface for the reusable oximeter and otherwise be a standard urinary catheter. This method and device for urethral pulse oximetry may be used in conjunction with any of the other embodiments detailed herein or may be a stand-alone device in and of itself.

DETAILED DESCRIPTION OF THE PREFERRED EMBODIMENTS

I. Device: Automated Urine Output Measurement
II. Indications for Use (IFU): Any condition requiring urine output monitoring
III. Preferred Methods for Use:
  a. Upon placement of a Foley catheter, ideally with a temperature sensor or intra-vesicular sensor/probe, the receptacle component of the Automated Urine Output Measurement system is attached to the output tubing
  b. The receptacle is attached to a stationary object, or the patient themselves and the data ID for the receptacle is entered into the RFID reader, which may be centralized and capable of querying all Automated Urine Output Measurement receptacles within a predefined range or area
  c. The RFID reader then queries, and optionally powers, the RFID chip within the receptacle which reports the fluid level based on the impedance, conductance or other electrical properties of sensors within the bag d. This data is transmitted to centralized data collection point where it may be monitored by an individual e. If certain thresholds are not met, ie 30 cc/hr urine output, local alarms (ie a beeping) or remote alarms (ie an alert at the centralized monitoring station) may be triggered f. The information obtained from the receptacle may be used in a feedback loop to automate the delivery and/or extraction of fluids and/or medicines from the patient to optimize therapy g. In conjunction with urine output measurement the healthcare professional may also attach an oximeter to a specifically designed site on the urinary catheter in order to obtain pulse oximetry measurements h. Once the measurements have been completed, the oximeter may be reused (or disposed of) and the urinary catheter either removed or kept in place In its preferred embodiment, the novel access system involves the use of a puncturing instrument in conjunction with a sensor at, or near, the tip of the instrument. This sensor may be capable of detecting changes within its environment in order to report that it has passed from the subcutaneous tissues into the desired cavity, space or tissue. For example, a novel peritoneal access catheter is envisioned which is capable of detecting differences between the vascular, extraperitoneal, intestinal and intraperitoneal spaces. This sensor may detect 1) changes in the physical properties surrounding the instrument such as pressure, acceleration, forces or other physical properties, 2) chemical changes surrounding the instrument, ie the presence or absence of compounds such as albumin, hemoglobin, glucose or the pH or other chemical properties, or 3) changes in the electrical properties such as conductance, resistance, impedance, capacitance, etc. of the tissues 4) changes in the acoustic or vibratory properties of the tissues, 5) changes in optical properties such as refraction of light within the tissue, or 6) changes in any other parameter that is able to be sensed via a sensor placed on, in, within or otherwise attached to or in communication with said instrument.

In any of the embodiments, as well, the sensing element of said device may be incorporated in instrument itself, may be introduced along with the instrument or may be external to the instrument and communicate through a channel in said instrument. In the ideal embodiment, the sensor is incorporated into either in the instrument or its introducer and is able to provide immediate, definitive feedback that the correct body cavity has been accessed. For example, the electrical properties of blood are different from that of air, the epidermis, the subcutaneous space, the fascia and the adventia of the vessel. Thus, in accessing the femoral artery, for instance, one can slowly insert the arterial access device (ie a catheter with a sharp insertion trocar/needle) which incorporates a sensor in the catheter or insertion trocar/needle (in this case electrical) which will immediately report a change in the sensed parameter (in this case inductance, resistance, capacitance, etc.) indicating that the vessel has been entered. This same reading can then them be monitored continuously as the instrument is manipulated (ie the catheter is slid over the trocar/needle into the vessel) to ensure that the instrument does not migrate during manipulation and remains within the desired space.

Another embodiment comprises the use of heat differentials to guide a catheter/needle to the appropriate space/tissue. For example, by placing a cold pack on the skin over the femoral artery, a temperature differential will exist with the warmest location being in the intravascular space. A temperature sensing catheter can be guided to the warmest location which would be inside the vessel.

This sensing technique may be employed with virtually any invasive instrument to ensure correct placement via detection of changes in any of the aforementioned parameters (i.e. physical, chemical, thermal, electrical, acoustic/vibratory, optical or other parameter capable of being sensed) with the only requirement being that the target tissue or space within the body must have a sufficiently distinct sensor reading that it may be distinguished from its surrounding tissues. These invasive instruments may include, but are not limited to instruments, catheters or devices intended to access the following spaces/tissue: peritoneal cavity or fluid (ie paracentesis or peritoneal lavage), vascular fluid or space (arterial catheter, intravenous catheter, etc.), cerebrospinal fluid or space, pleural or pulmonary fluid or space (ie chest tubes), pericardial or cardiac space or tissue, urologic fluid or space (ie suprapubic catheters), gynecologic access (ie fallopian tubes or ovaries), gastrointestinal fluid or space (ie nasogastrostomy or gastrostomy tubes), ocular or bulbar tissues or spaces, neurological tissue or space (ie brain biopsy instruments), pathological tissue or space (ie abscess, hematoma, cyst, pseudocyst), bone marrow tissue or space, or any other tissues or spaces that may be accessed minimally invasively, percutaneously or through a natural orifice.

The sensing element may be disposable or reusable. The sensing element may be incorporated reversibly or irreversibly into the instrument itself, into the instrument's sheath, into the instrument's trocar, or kept external to said instrument with movement of gases, fluids or solids down the length of the instrument to the externally located sensor continuously or upon activation. Said sensor may also communicate wirelessly from the instrument to an external receiver removing the requirement for a tethering cord and allowing for a disposable and reusable component. The controller/reader may alert the user that access has been obtained through tactile, auditory, visual or any other _stimuli. The sensing may occur continuously or only upon command by the user (ie once they suspect that they are in the tissue or cavity).

FIGS. 9A-9D show side views of the sensor incorporated into the instrument. In this image, the instrument 91 (in this case a needle or trocar) contains a sensor 92 at its tip which may intermittently or continuously provide information to the user to indicate plane of insertion. In this illustration, the instrument is shown passing through the subcutaneous tissues and muscular layers 93 and entering the cavity 95 without harming or penetrating the tissues beneath. Examples where this illustration apply include: peritoneal cavity access, pleural cavity access, cerebrospinal cavity access, etc. In each of these cases, entrance into the space may be required but the underlying tissues (the intestines/liver, lungs and spinal cord/brain, respectively) are sensitive and a sensing technology to prevent over-insertion would be a significant advance in the state of the art. In addition to the sensors detection of 1) changes in the physical properties surrounding the instrument such as pressure, acceleration, forces or other physical properties, 2) chemical changes surrounding the instrument, ie the presence or absence of compounds such as albumin, hemoglobin, glucose or the pH or other chemical properties, or 3) changes in the electrical properties such as conductance, resistance, impedance, capacitance, etc. of the tissues 4) changes in the acoustic or vibratory properties of the tissues, and/or 5) changes in optical properties such as refraction of light within the tissue to detect instrument entrance into the cavity, 6) and/or changes in the thermal properties of the tissues the same sensor, or another sensor, may be capable of detecting other components that signal an issue may have occurred during entry. For example, with the peritoneal catheter example, the sensor, or another sensor, may be able to detect the presence of fecal matter or blood which would indicate that even though the cavity may have been entered, the catheter may been over-inserted or is not in its correct position. This positive feedback related to instrument entry and negative feedback with respect to possible incorrect positioning of the instrument, in combination, provide confidence to the user not only that the correct cavity, space or tissues have been accessed but that no complications have arisen during the access procedure.

One example of this embodiment is a peritoneal access catheter with an electrical inductance sensor at its tip. The subcutaneous space has a different inductance compared to the peritoneal space which also has a different inductance than the intestinal lumen. In accessing the peritoneal cavity, then, the catheter may be advanced until the subcutaneous tissue inductance readings change to the peritoneal cavity inductance levels. Once the peritoneal cavity is sensed, based on the change in electrical properties, the catheter then provides feedback that the cavity has been accessed. In the event that the catheter is over-inserted into the bowel, the inductance will be dramatically lower than that found in the subcutaneous tissue or peritoneal space and this complication can be rapidly reported. In addition, iron-rich blood has a higher inductance than any of the other tissues and exposure to concentrated blood can be quickly reported if the catheter experiences this fluid. The cutoff may be set, as well, so that dilute blood does not trigger the sensor since minor capillaries may be ruptured in the normal access procedure. This same technique may be used, in reverse, to purposefully access the vascular space. In fact, most tissues have characteristic electrical properties and virtually any tissue, cavity or space may be accessed through monitoring for this signal during instrument insertion. This is just one embodiment and the access device may be used to access any body tissue, space, or cavity and may do so with feedback from any of the sensors detailed above or any other sensing technology.

FIGS. 10A-10E are side views of the sensor incorporated into removable insertion trocar. In this instance, the sensor is not incorporated into the catheter itself, but is instead coupled with an insertion tool, in this case a central insertion trocar 107. Once the tissue, space, or cavity has been accessed, the insertion trocar may be removed 8 and the catheter advanced or left in place to allow access to the tissue or space for the intervention.

FIGS. 11A-11E illustrate side views of the sensor 118 incorporated into removable sheath 119. In this embodiment, the sheath sensor 118 reports entry into the space then the access instrument 1110 is left in the cavity 1111 while the insertion sheath 119 is removed. This embodiment is particularly appealing in instance where, once access is confirmed, future confirmation is not required since the sensor is removed along with the sheath. This embodiment is most useful, then, in instances where the instrument 1110 will remain in place for a long period of time (i.e. an implantable device with long-term action) or where the desired profile of the instrument 1110 is sufficiently small that inclusion of the sensor 118 into the instrument 1110 itself becomes technically challenging and economically impractical.

FIGS. 12A-12C demonstrate side views of the External Reader attached to the access device. In this embodiment, the external reader 1212 may have a display 1213 or some other form of alert to let the user know that the access device has entered the correct cavity, or in which cavity the sensor currently resides. In its optimal embodiment, the sensor will provide information related to the tissue surrounding the sensor continuously and in real-time so that informed decisions to advance or retract the access device may be made. This illustration depicts the sensor incorporated within a removable insertion trocar, but it is important to note that this external reader and any other method of reporting device position to the user may be used with any of the sensing technologies described in this text or illustrated in these drawings.

FIGS. 13A-13D illustrate side-views of the continuous reader incorporated into access device. In this embodiment, the integrated reader 1314 may have a display 1315 or some other form of alert to let the user know that the access device has entered the correct cavity, or in which cavity the sensor currently resides. As with the external reader of FIG. 12, in its optimal embodiment, the sensor will provide information related to the tissue surrounding the sensor continuously and in real-time so that informed decisions to advance or retract the access device may be made. This illustration depicts the sensor incorporated within a removable insertion trocar, but it is important to note that this external reader and any other method of reporting device position to the user may be used with any of the sensing technologies described in this text or illustrated in these drawings. As with any of the embodiments described, the sensing device (here shown as the insertion trocar), may be disposable or reusable.

FIGS. 14A-14D illustrate side-views of the intermittent reader incorporated into the access device. In this embodiment, the integrated reader may have a display or some other form of alert to let the user know that the access device has entered the correct cavity, or in which cavity the sensor currently resides. As with the integrated reader of FIG. 13, in its optimal embodiment, the sensor will provide information related to the tissue surrounding the sensor, but will do so only when activated, in this instance via deployment of a reversible a push-button 1416 at the end of the insertion device. This intermittent reading may give exact tissue location information, as well, and may be deployed repeatedly. This embodiment is particularly appealing for sensing technologies, ie optical, that may produce heat or other potentially harmful byproducts and should, ideally, only be activated for brief periods of time. As with other embodiments, informed decisions to the advancement or retraction of the access device may be made. This illustration depicts the sensor incorporated within a removable insertion trocar, but it is important to note that this external reader and any other method of reporting device position to the user may be used with any of the sensing technologies described in this text or illustrated in these drawings. As with any of the embodiments described, the sensing device (here shown as the insertion trocar), may be disposable or reusable.

FIGS. 15A-15E illustrate side-views of the sensor incorporated into a catheter, this time again with the central trocar embodiment. In this embodiment, as with FIG. 11, a sensor may be incorporated into the external sheath surrounding an insertion trocar. In contrast, though, in this embodiment the insertion trocar may be removed and the sensor-containing sheath 1517 may remain within the cavity. This embodiment is particularly useful for catheter insertion and advancement (as illustrated in successful illustration from top to bottom). Using the sensor at the tip, catheter position may be continuously or intermittently assessed while it is advanced thereby ensuring that the catheter is not only in position when the trocar is removed, but that it remains within the correct cavity while it is advanced. The catheter or sheath may be single or multiple lumen catheter and may employ a sensor incorporated into instrument or an external sensor. The catheter may also use additional sensors or lumens or other communication means to external sensors in order to provide the desire intervention or therapy. One preferred embodiment of this device describes a method of accessing the peritoneal cavity with a catheter. In this embodiment, the sensor-containing catheter may be advanced using the central trocar as a stiffening element. This insertion procedure may employ a blunt dissecting instrument or may utilize the Seldinger technique (or modification thereof). Once the catheter or sheath begins to move through the tissues, though, the sensor at the tip may report position to the user, either intermittently or—ideally-continuously, indicating which tissues are surrounding the sensor. Once the peritoneal cavity has been accessed, in this embodiment, the reader, either external or integrated within the access device, reports that the cavity has been accessed via visual, auditory or tactile stimuli. The central trocar may then be removed and the catheter advanced, once again during continuous monitoring by the sensor in its optimal embodiment. If the catheter moves from the peritoneal cavity (ie into subcutaneous tissues, muscle, bowel or any other organ) or becomes surrounded by another fluid (blood, urine, etc.) then the sensor may report the change and indicate to the user that the device is no longer optimally placed and that further intervention (whether it be simply adjusting the catheter or performing further investigation) is required. Using this device and method, the user may ensure precise and consistent access to the peritoneal cavity not only upon insertion but for the duration of the placement of the device and through any required manipulations.

FIG. 16 details the embodiment wherein intravenous fluid delivery may be automated, or manually adjusted, based on feedback from one or more sensors. In this embodiment, the infusion catheter 1618 may preferably have a sensor to aid in insertion, but this is not necessary for this invention. In the ideal embodiment, the infusion catheter also is used to detect the parameters used to optimize therapy, namely electrocardiograph monitoring, electroencephalograph monitoring, pulse oximetry (either internally or peripherally), blood pressure, central venous pressure, cardiac output, cardiac stroke volume, cardiac rate, blood flow (i.e. in superior mesenteric, celiac, renal or other arteries), total circulating blood volume, pressure in veins (particularly those that empty, into the IVC, i.e. femoral vein), pressure in arteries (particularly those distal to the aorta, i.e. the femoral artery), blood oxygenation (i.e. in rectal mucosa, peripheral fingers arid toes, etc.), whole body oxygen consumption, pH, arterial pO2, or any other parameter that shows a measurable change with intravascular volume overload. Additional catheters, here envisioned as a peripherally inserted central catheter (PICC) 1619, or bladder catheter 1620, or additional sensors on this infusion catheter may be used to monitor these, or other, parameters, though to optimize the infusion rate and achieve euvolemia without fluid overload or dehydration. This information may then be transmitted to a central controller 1621, which integrates all of this information to determine the flow of intravenous fluid. This may be used to achieve or maintain euvolemia (ie in sepsis, hemorrhagic shock, etc.) or to maximize infusion for delivery of a therapeutic agent, i.e. chilled fluid and/or solids to achieve hypothermia. The sensor or sensors, whether cables/ catheters or percutaneous monitoring technologies wired or wireless, may also be disparate from the infusion line so long as the information from this sensor or sensors is transferred to the control unit in order to optimize fluid flow. In this embodiment, as well, the device of the current invention may or may not incorporate the access sensor, but may utilize sensors to optimize therapy. One example of such a device is a peripheral venous, central venous or arterial catheter that is capable of maintaining hydration without causing fluid overload. Said catheter may incorporate a sensor which may detect central venous pressure, total circulating blood volume, peripheral venous pressure, cardiac output or osmolarity, and/or solute concentrations (ie chloride, sodium, etc.) in order to prevent fluid overload. The sensor may also be external to said catheter, so long as the output of said sensor is capable of controlling fluid flow through the catheter. In this embodiment, said fluid flow is controlled by the output of said sensor which is integrated by a fluid flow control unit which alters the rate of fluid flow based on this output. This embodiment may allow the user to bolus large volumes of fluids or solids into the vascular space in order to rehydrate, induce hypothermia or induce hypothermia, or deliver a therapeutic agent or maintain blood pressure in sepsis. In addition, this technology may provide a fully automated mechanism to optimize fluid flow into the vessel without fluid overloading the patient. Without this automated fluid delivery coupled to hemodynamic parameter monitoring, the patient is in danger of dehydration or fluid overload from any vascular infusion. This technology may also be applied to liquid or solid infusion into any body cavity or space in so long as the fluid flow is automated based on feedback from sensors within the body (ideally incorporated into the catheter itself) in order to optimize the volume of infusion. This device and method of automating fluid flow based on hemodynamic sensor-based feedback may also be used to generate intravenous hypothermia. In its current state, IV hypothermia induction is limited due to concerns of fluid overload. If the hemodynamic parameters of the patient can be measured and fluid flow directly or indirectly controlled based on the output of these measurements, the volume of fluid can be maximized while ensuring hemodynamic instability. In this embodiment, the sensor may be, ideally, incorporated within the catheter and fluid flow into the vasculature may be tailored based on central venous pressure, total circulating blood volume, peripheral venous pressure, cardiac output or osmolarity, and/or solute concentrations (ie chloride, sodium, etc.) in order to prevent fluid overload. In its optimal embodiment, the fluid infusion catheter also may function as a thermodilution cardiac output sensor such that the same fluid that is used to generate hypothermia may also be used to detect cardiac output. This information may then be relayed, either directly or indirectly, back to the fluid infusion controller to increase, decrease or even halt fluid flow based on these parameters, ie if cardiac output is low and venous pressure or total circulating volume is low, the patient has a low circulating volume and large volumes of fluid may be safely delivered. If the cardiac output is normal, fluid may also be safely delivered, but the cardiac output must be monitored to ensure that it does not begin to decrease (an indication of fluid overload). This same system may be used to infuse normal fluids or hypothermic fluids to sepsis patients or patients requiring intensive maintenance of their hemodynamic status. Sepsis patients that are aggressively monitored do much better than those that are not. This is very nurse-intensive, though, so a system that provides automated optimal fluid infusion based on sensed parameters to ensure that fluid overload does not occur and that fluid infusion is not insufficient. This device providing for the automated sensor-based input to control fluid flow and method of delivering fluid using this system may be applicable to a wide range of conditions and should not be limited to the narrow scope of the conditions requiring fluid infusion described here.

While this description has focused largely on the method and device for peritoneal insertion, this same procedure and method may be used to access any body cavity, tissue or space reliably and consistently with confidence. In using this technology, clinician's may be confident that their instrument resides in its desired space without the requirement for complex instrumentation or costly imaging techniques. For example, in its preferred embodiment this method and device may be used in conjunction with any access device that currently requires imaging to confirm placement, but without the need for ionizing radiation. Examples of such devices include nasogastric tubes, central venous lines, chest tubes, feeding tubes, etc.

Communications between the sensor and display or instrument control unit may also be done wirelessly, ie via RFID or Bluetooth. In the instance where the catheter is a dual lumen catheter, one lumen may be used for fluid delivery while the other may be used for fluid return and a temperature and/or pressure sensor may be incorporated along its length, ideally closer to the fluid return tubing than the fluid delivery tubing.

Furthermore, the logic controller of the present invention may provide improved safety by monitoring for any of the deleterious changes expected with excess fluid flow i.e. into the peritoneal cavity or vascular space. Examples of monitored parameters that may signal a warning or automatically result in an adjustment to rate of fluid infusion/extraction and/or fluid temperature include: electrocardiograph monitoring, electro-encephalograph monitoring, pulse oximetry (either internally or peripherally), peritoneal cavity compliance, intrathoracic pressure, intraperitoneal pressure, bladder pressure, rectal pressure, cardiac output, cardiac stroke volume, cardiac rate, blood flow (i.e. in superior mesenteric, celiac, renal or other arteries), pressure in veins (particularly those that empty into the IVC, i.e. femoral vein), pressure in arteries (particularly those distal to the aorta, i.e. the femoral artery), blood oxygenation (i.e. in rectal mucosa, peripheral fingers and toes, etc.), whole body oxygen consumption, pH and arterial pO2 and any other parameter that shows a measurable change once the peritoneal or vascular spaces have been overloaded. These parameters, in particular, have been found to change with increases in peritoneal pressure with significantly negative impact on each parameter found at 40 mmHg, thus monitoring for these changes in conjunction with the peritoneal infusion catheter of the present invention will allow for even greater safety with peritoneal infusion. These parameters may be measured a variety of ways and the data transmitted either wirelessly or via wires to the logic controller in order to alert the healthcare provider or to automatically adjust the fluid flow/temperature in order to optimize both the flow of the peritoneal fluid and patient safety.

While most of these embodiments have been written focusing on certain embodiments, i.e. a catheter technology, the invention may be used with any instrument that demands precise access to tissues, body cavities or spaces and/or requires automated, sensor-based intervention or therapy.

DETAILED DESCRIPTION OF THE PREFERRED EMBODIMENTS

I. Device: Peritoneal Access Safety System (PASS)
II. Indications for Use (IFU): Any intervention requiring peritoneal access
III. Preferred Methods for Use:
  a. Upon presentation with a condition fitting the criteria for IFU, the device of the present invention will be obtained and the patient will be prepared for paracentesis.
  b. The access system will then be advanced through the subcutaneous and deeper tissues slowly while the reader is closely observed to indicate the depth of the puncture.
  c. The reader indicates depth of puncture, ideally, based on the unique electrical signature (impedance, resistance, capacitance, etc.) of the tissue surrounding the sensor.
  d. Once the reader indicates that the cavity has been accessed, advancement ceases and the central insertion trocar may be removed and/or the catheter advanced.
  e. The soft, blunt-tipped catheter may be advanced slowly, once again while the position reader is observed.
  f. Once the catheter has been inserted to its desired depth the position is once again checked and, if the catheter has been correctly inserted, the intervention is performed.
  g. If the catheter position is not correct, corrective measures may be taken to ensure correct positioning prior to any intervention.
  h. Optionally, but preferably, the position sensor may continuously monitor position to ensure that the catheter does not migrate during the intervention.
  i. Optionally, but preferably, as well, the sensor may be used to indicate the occurrence of complications (ie presence of blood) with any intervention
  j. Optionally, but preferably, as well, the catheter may contain other sensor technology, ie pressure and/or temperature sensors, to guide therapeutic intervention such as optimization of peritoneal filling with peritoneal hypothermia or resuscitation.

What is claimed is:

1. An apparatus for accessing a body space within a body, comprising:
  an elongate device configured for insertion into the body;
  two linear electrodes positioned on the elongate device such that the two linear electrodes each has a length which extends axially while next to one another along an axial direction and while separated from one another by spacing which also extends in the axial direction along the elongate device between each length such that the spacing is defined to extend axially in an elongated manner with nearly parallel sides and each length is circumferentially spaced apart from one another and are positioned to contact tissue which is adjacent to the elongate device during advancement of the elongate device into the body and to detect an electrical property of the tissue;
  a controller in communication with the two linear electrodes, wherein the controller is configured to receive one or more signals from the tissue in contact with a first portion of each length of the two linear electrodes and detect a change in the electrical property in a continuous manner along the length of each electrode as the elongate device is advanced into contact with a second portion of each length of the two linear electrodes, and wherein the controller is further configured to continuously determine a position of the elongate device relative to the body space based upon the change detected in the electrical property along the length of the elongate device as the elongate device is advanced.

2. The apparatus of claim 1 wherein the controller is further configured to determine whether the body space has been accessed based upon the change detected in the electrical property.

3. The apparatus of claim 1 wherein the controller is further configured to provide an alert when the body space has been accessed.

4. The apparatus of claim 1 wherein the controller is further configured to determine when the elongate device should be advanced or retracted within the tissue.

5. The apparatus of claim 1 wherein the controller is further configured to provide an indication on when the elongate device should be advanced within the tissue.

6. The apparatus of claim 1 wherein the two linear electrodes comprise linear electrodes along a distal portion of the elongate device.

7. The apparatus of claim 1 wherein the two linear electrodes are configured to detect an electrical property of an environment surrounding the two linear electrodes.

8. The apparatus of claim 1 wherein the two linear electrodes are configured to detect a conductance property of the tissue.

9. The apparatus of claim 1 wherein the two linear electrodes are configured to detect an impedance property of the tissue.

10. The apparatus of claim 1 wherein the elongate device comprises a nasogastrostomy tube.

11. The apparatus of claim 1 further comprising a nasogastrostomy tube positionable in proximity to the elongate device.

12. The apparatus of claim 1 further comprising a nasogastrostomy tube defining a lumen into which the elongate device is positionable.

13. The apparatus of claim 1 wherein the controller is further configured to detect the change in the property continuously or intermittently.

14. The apparatus of claim 1 further comprising a fluid delivery device in communication with the controller, wherein the fluid delivery device is configured to deliver or extract a fluid from the body.

15. The apparatus of claim 14 wherein the fluid delivery device is configured to deliver or extract the fluid automatically or manually.

16. The apparatus of claim 1 wherein the elongate device employs a blunt dissecting instrument.

17. The apparatus of claim 1 further comprising a sensor positioned along the elongate device at a distance in the axial direction from the two linear electrodes, wherein the sensor is configured to detect a parameter which is different from the two linear electrodes.

18. The method of claim 1 wherein the two linear electrodes each has a continuous length which extends axially in an elongated manner with nearly parallel sides while next to one another along the axial direction.

19. The method of claim 1 wherein the length of each linear electrode is longer than a diameter of the elongate device.

20. A method for accessing a body space within a body, comprising:

advancing an elongate device into the body while contacting tissue adjacent to the elongate device during advancement via two linear electrodes each having a length which extends axially while next to one another along an axial direction and while separated from one another by spacing which also extends in the axial direction along the elongate device between each length such that the spacing is defined to extend axially in an elongated manner with nearly parallel sides and each length is circumferentially spaced apart from one another;

receiving one or more signals from the two linear electrodes and from the tissue in contact with a first portion of each length of the two linear electrodes which is adjacent to the elongate device;

detecting a change in an electrical property in a continuous manner along the length of each electrode via a controller in communication with the two linear electrodes as the elongate device is advanced into contact with a second portion of each length of the two linear electrodes; and determining continuously via the controller a position of the elongate device relative to the body space based upon the change detected in the electrical property along the length of the elongate device as the elongate device is advanced.

21. The method of claim 20 wherein determining via the controller comprises determining whether the body space has been accessed based upon the change detected in the electrical property.

22. The method of claim 20 further comprising providing an alert when the body space has been accessed.

23. The method of claim 20 further comprising determining when the elongate device should be advanced or retracted within the tissue.

24. The method of claim 20 further comprising providing an indication on when the elongate device should be advanced within the tissue.

25. The method of claim 20 wherein detecting the change comprises detecting an electrical property of an environment surrounding the two linear electrodes.

26. The method of claim 20 wherein detecting the change comprises detecting a conductance property of the tissue.

27. The method of claim 20 wherein detecting the change comprises detecting an impedance property of the tissue.

28. The method of claim 20 wherein advancing the elongate device comprises advancing a nasogastrostomy tube.

29. The method of claim 20 wherein advancing the elongate device comprises advancing the elongate device in proximity to a nasogastrostomy tube.

30. The method of claim 20 wherein advancing the elongate device comprises advancing the elongate device within a lumen defined through a nasogastrostomy tube.

31. The method of claim 20 wherein detecting the change comprises detecting the change continuously or intermittently in the property.

32. The method of claim 20 further comprising delivering or extracting a fluid from the body via a fluid delivery device in communication with the controller.

33. The method of claim 32 wherein delivering or extracting the fluid comprises automatically or manually delivering or extracting the fluid.

34. The method of claim 20 wherein the elongate device employs a blunt dissecting instrument.

35. The method of claim 20 wherein the elongate device further comprises a sensor positioned along the elongate device at a distance in the axial direction from the two linear electrodes, and wherein the sensor is configured to detect a parameter which is different from the two linear electrodes.

36. The method of claim 20 wherein the two linear electrodes each has a continuous length which extends axially in an elongated manner with nearly parallel sides while next to one another along the axial direction.

37. The method of claim 20 wherein the length of each linear electrode is longer than a diameter of the elongate device.

* * * * *